(12) United States Patent
Liu et al.

(10) Patent No.: US 11,730,742 B2
(45) Date of Patent: Aug. 22, 2023

(54) PHARMACEUTICAL USE OF THIOPHENE [3,2-D] PYRIMIDINE-4-KETONE COMPOUND

(71) Applicant: SHANGHAI INSTITUTE OF MATERIA MEDICA, CHINESE ACADEMY OF SCIENCE, Shanghai (CN)

(72) Inventors: Hong Liu, Shanghai (CN); Jia Li, Shanghai (CN); Jiang Wang, Shanghai (CN); Yi Zang, Shanghai (CN); Jian Li, Shanghai (CN); Jingya Li, Shanghai (CN); Dandan Sun, Shanghai (CN); Hualiang Jiang, Shanghai (CN); Kaixian Chen, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 182 days.

(21) Appl. No.: 16/978,563

(22) PCT Filed: Mar. 8, 2019

(86) PCT No.: PCT/CN2019/077560
§ 371 (c)(1),
(2) Date: Sep. 4, 2020

(87) PCT Pub. No.: WO2019/170157
PCT Pub. Date: Sep. 12, 2019

(65) Prior Publication Data
US 2021/0015824 A1 Jan. 21, 2021

(30) Foreign Application Priority Data

Mar. 9, 2018 (CN) .......................... 201810194967.6

(51) Int. Cl.
*A61K 31/5377* (2006.01)
*A61K 31/519* (2006.01)
*A61P 1/16* (2006.01)

(52) U.S. Cl.
CPC ........ *A61K 31/5377* (2013.01); *A61K 31/519* (2013.01); *A61P 1/16* (2018.01)

(58) Field of Classification Search
CPC .............. A61K 31/519; A61K 31/5377; A61K 9/0019; A61K 9/0021; A61K 9/0043; A61K 9/0048; A61K 9/0053; A61K 9/0095; A61K 9/02; A61K 9/06; A61K 9/2004; A61K 9/4841; A61K 9/7007; A61K 9/7015; A61P 1/16
See application file for complete search history.

(56) References Cited

U.S. PATENT DOCUMENTS

| 9,045,491 | B2 | 6/2015 | Liu et al. |
| 2012/0121530 | A1 | 5/2012 | Klein et al. |
| 2014/0323466 | A1* | 10/2014 | Liu .......................... A61P 3/10 |
| | | | 544/278 |
| 2016/0354380 | A1 | 12/2016 | Dugi et al. |
| 2019/0031678 | A1 | 1/2019 | Liu et al. |

FOREIGN PATENT DOCUMENTS

| CA | 3018800 A1 | 9/2017 |
| CN | 101817833 A | 9/2010 |
| CN | 102311448 A | 1/2012 |
| CN | 102659813 A | 9/2012 |
| CN | 103130819 A | 6/2013 |
| CN | 107216340 A | 9/2017 |
| EP | 2786998 A1 | 10/2014 |
| EP | 3434678 B1 | 1/2021 |
| WO | 2004/014916 A1 | 2/2004 |
| WO | WO-2009147125 A1 | 12/2009 |
| WO | WO-2011118976 A2 | 9/2011 |
| WO | WO-2013078765 A1 | 6/2013 |
| WO | WO-2019170157 A1 | 9/2019 |

OTHER PUBLICATIONS

English Translation of the International Search Report corresponding to PCT/CN2019/077560 dated Jun. 10, 2019; 4 pages.
Yu, Yuan et al., "Progress of the Correlation between DPP-4 and Chronic Liver Disease," *Chinese Journal of Gastroenterology and Hepatology*, see, Abstract in English; (Sep. 30, 2015) 24(9):1152-1154.
English translation Office Action with Search Report in corresponding RU Appl 2020133048/04 dated Jul. 7, 2021 (13 pages).
Itou, Minoru et al., "Dipeptidyl peptidase-4: A key player in chronic liver disease," *World J Gastroenterol* (Apr. 21, 2013) 19(15):2298-2306 abstract, "Non-alcoholic fatty liver disease," section, conclusion.

(Continued)

*Primary Examiner* — Sarah Pihonak
(74) *Attorney, Agent, or Firm* — Mintz Levin Cohn Ferris Glovsky and Popeo, P.C.

(57) ABSTRACT

Disclosed is use of a thieno[3,2-d]pyrimidin-4-one compound represented by general formula (I). Definition of each substituent is as stated in the description and claims, and the compound is used for preparing medicines for treating and/or preventing liver fibrosis and related diseases or preparing a DPP-4 inhibitor, or is used as a DPP-4 inhibitor.

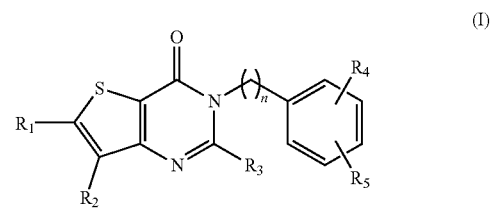

(I)

9 Claims, 6 Drawing Sheets

(56) References Cited

OTHER PUBLICATIONS

Deng et al. (Jan. 1, 2011) "The highly potent and selective dipeptidyl peptidase IV inhibitors bearing a thienopyrimidine scaffold effectively treat type 2 diabetes", Eur J Med Chem, 46(1):71-76.
Extended European Search Report for Application No. EP 19763907.3, dated Nov. 18, 2021, 17 pages.
Kaji et al. (2014) "Dipeptidyl peptidase-4 inhibitor attenuates hepatic fibrosis via suppression of activated hepatic stellate cell in rats", Journal of Gastroenterol, 49(3):481-491.
Mahmoud et al. (Mar. 1, 2018) "The Beneficial Effects of Sitagliptin, a Dipeptedyl Peptidase-4 (DPP-4) Inhibitor on Experimentally Induced Non-Alcoholic Fatty Liver Disease in Rats", The Medical Journal of Cairo University, vol. 86, No. 2, pp. 1065-1076.
Marques et al. (2017) "Dipeptidyl peptidase IV (DPP-IV) inhibition prevents fibrosis in adipose tissue of obese mice", Biochimica Et Biophysica Acta, 1862(3):403-413.
English translation Office Action in corresponding JP Appl 2020-547088 dated Oct. 28, 2021 (3 pages).
Wang, Xiao-Yu et al., "Linagliptin mediated DPP-4 inhibition ameliorates inflammation and fibrosis in models of NASH and biliary fibrosis," Hepatology (Oct. 2014) Documents indicating well known arts, vol. 60, No. 4, Suppl. 1, Sp. Iss. SI, pp. 574A-575A, AASLD Abstract 774 only.
Wang, Xiaoyu et al., "Oral hepatotropic DPP4 inhibitors attenuate NASH and bilary fibrosis in part through macrophage modulation," Hepatology (Oct. 2015) Documents indicating well known arts, vol. 62, Supp. Suppl. 1, pp. 884A, AASLD Abstract 1376 only.
Yamamoto, Naaki et al., "Dipeptidyl Peptidase-4 (DPP IV) Inhibitor Prevents Liver Fibrosis and Preneoplastic Lesions in Rat Liver Cirrhosis Induced by Choline-Deficient L-Amino Acid-Defined Diet;" Hepatology (2011) Documents indicating well-known arts, vol. 54, No. 4, Suppl, pp. 745A-746A, AASLD Abstract 814 only.
Baumeier, Christian et al. "Elevated hepatic DPP4 activity promotes insulin resistance and non-alcoholic fatty liver disease" Molecular Metabolism, Aug. 4, 2017, pp. 1254-1263.

* cited by examiner

PHARMACEUTICAL USE OF THIOPHENE [3,2-D] PYRIMIDINE-4-KETONE COMPOUND

TECHNICAL FIELD

The invention relates to a pharmaceutical use of thieno [3,2-d]pyrimidin-4-one compounds, and in particular to use in the manufacture of a medicine for treating and/or preventing liver fibrosis and related diseases.

BACKGROUND TECHNIQUE

Hepatic fibrosis (Liver fibrosis) is a chronic damage repair reaction that occurs in the liver after various pathogenic factors affect the liver. Viral hepatitis, chemical poison or drug-induced liver disease, alcoholic/non-alcoholic fatty liver, autoimmune liver disease, congenital metabolic disease and the like may cause liver fibrosis. Non-alcoholic steatohepatitis (NASH) and liver fibrosis refer to pathological changes caused by the abnormal hyperplasia of intrahepatic connective tissue and chronic liver damage triggered by a variety of pathogenic factors, are manifested as excessive abnormal deposition of extracellular matrix components in the liver and affect the function of the liver, and are the necessary stages for the development of chronic liver disease to cirrhosis. Any liver injury has a process of liver fibrosis in the process of liver repair and healing. If the damage factor cannot be removed for a long time, long-term fibrosis will develop into cirrhosis. There are currently more than 200 million patients with various types of liver diseases in China, including about 93 million hepatitis B virus carriers, about 40 million hepatitis C virus carriers, and about 120 million patients with fatty liver. With the changes in Chinese dietary structure and living habits, the incidence of fatty liver has soared in recent years, and the onset of the disease gradually occurs at younger age. The prevalence rate of fatty liver in children is as high as 2.6%, and the young are only 6 years old. 70% of patients with long course of chronic liver disease have liver fibrosis, and 25% of liver fibrosis further develops into cirrhosis in 10 years, of which 5% may develop into liver cancer. Liver disease not only brings great suffering to patients and families, but also causes an extremely heavy economic burden to society.

The pathogenesis of non-alcoholic steatohepatitis (NASH) and liver fibrosis is more complicated and is related to various enzymes and receptors. It is currently believed that liver fibrosis is a reversible pathological process of abnormal deposition of fibrous connective tissue in the liver caused by the imbalance between the production and degradation of extracellular matrix (ECM) such as collagen in the liver, reflecting a dynamic balance process of liver repair and scar formation. Although the research on the pathogenesis of liver fibrosis is getting deeper, there is still no effective treatment to reverse liver fibrosis, and the development of anti-liver fibrosis drugs is very slow. At present, the FXR agonist obeticholic acid (OCA) is the most clinically used to treat non-alcoholic steatohepatitis (NASH) and liver fibrosis. Only obeticholic acid was quickly approved by the FDA for the treatment of cholestatic liver cirrhosis in June 2016. The steroidal compound obeticholic acid is a FXR agonist of farnesoid X receptor of the nuclear receptor family. As an endogenous bile acid receptor, FXR is widely involved in the regulation of bile acid, sugar, lipid metabolism, inflammation and other processes. After being agitated, FXR can indirectly inhibit the gene expression of CYP7A1 and inhibit the synthesis of bile acid, so as to treat primary cholestatic cirrhosis and relieve symptoms such as hepatic ascites caused by hepatic portal hypertension. The therapeutic research thereof on non-alcoholic steatohepatitis (NASH) has completed clinical phase III trial.

However, 70% of obese patients with type 2 diabetes have non-alcoholic fatty liver disease or NAFLD, and 30-40% patients have non-alcoholic steatohepatitis or NASH. Obeticholic acid has been shown to reduce insulin resistance in previous animal models. In the completed phase II trials for evaluating the effect of OCA on non-alcoholic fatty liver disease combined with type 2 diabetes, although the number of cases and the study time were relatively short, the results showed that OCA activated FXR, thereby improving the insulin sensitivity of patients with non-alcoholic fatty liver and diabetes. But the efficacy needs to be proved by larger clinical trials.

Dipeptidyl peptidase-4 (DPP-4) is an 110 kDa cell surface serine protease, also known as T cell surface antigen CD26. It is a multifunctional enzyme that exists in the cell membrane in the form of a homodimer. It can recognize oligopeptides whose second amino acid at the amino terminal is alanine (Ala) or proline (Pro), and cut and remove the first two amino acids at the amino terminal. The substrates that can be cut include growth factors, chemokines, neuropeptides and vasoactive peptides. Because it can cut GLP-1, it plays an important role in sugar metabolism. A number of DPP-4 inhibitors have been marketed for the treatment of type 2 diabetes. Currently, the DPPIV inhibitor evogliptin (South Korea) is undergoing phase I clinical trials in the United States for the treatment of NASH. Studies have shown that DPP-4 inhibitors have a good therapeutic effect in patients with diabetes mellitus accompanied by non-alcoholic fatty liver disease (NAFLD) and non-alcoholic steatohepatitis (NASH) during clinical use. Therefore, the development of drugs with better DPP-4 selectivity will undoubtedly have a good market prospect for the treatment of non-alcoholic fatty liver disease (NAFLD), non-alcoholic steatohepatitis (NASH) and liver fibrosis.

SUMMARY OF THE INVENTION

The purpose of the present invention is to provide a medicine for treating and/or preventing liver fibrosis and related diseases.

In one aspect of the present invention, it provides use of thieno[3,2-d]pyrimidin-4-one compound represented by the following general formula (I), pharmaceutically acceptable salt, solvate, stereoisomer, or tautomer thereof for manufacture of a medicament for treatment and/or prevention of liver fibrosis and related diseases, or for manufacture of a DPP-4 inhibitor or use as a DPP-4 inhibitor,

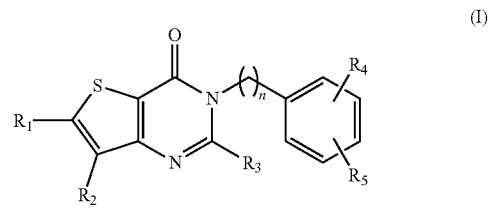

n is an integer from 1 to 3;

$R_1$ and $R_2$ are identical or different, and not hydrogen simultaneously, and each of $R_1$ and $R_2$ is independently H, halogen, $CBr_2H$, $CCl_2H$, $CF_2H$, cyano, $CF_3$, aldehyde group, $(CH_2)_mOR_6$, $(CH_2)_mNR_6R_7$,

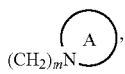

$(CH_2)_mCOOR_8$, $CONR_9R_{10}$, or

wherein, $R_1$ and $R_2$ can be optionally linked together to form C3-C6 alkylidene;

m is an integer from 0 to 3;

$R_6$ and $R_7$ are identical or different, and each of $R_6$ and $R_7$ is independently selected from H, C1-C6 linear or branched saturated or unsaturated hydrocarbyl, C3-C7 cyclic hydrocarbyl, C1-C3 alkoxy, 4-7 membered heterocyclic radical, C1-C4 alkyloyl RCO, C5-C7 aroyl ArCO, C1-C4 alkylsulfonyl $RSO_2$, C5-C7 arylsulfonyl $ArSO_2$, C5-C7 aroylmethylene, 5-7 membered heteroaroylmethylene, benzyl, pyridinedimethylene, C5-C7 aryl Ar or 5-7 membered heteroaryl; wherein, the C1-C6 linear or branched saturated or unsaturated hydrocarbyl is optionally substituted by one or more substituents selected from methylsulfonyl, cyclopropyl, hydroxy, C1-C3 alkoxy, C1-C3 alkoxycarbonyl, and epoxypropyl; the heterocyclic radical contains 1-3 heteroatoms selected from O, S and N, the methylene of the heterocyclic radical is optionally substituted by carbonyl or sulfonyl, or the heterocyclic radical is optionally substituted by one or more substituents selected from halogen, C1-C6 linear or branched hydrocarbyl, cyano, nitro, amino, hydroxy, hydroxymethyl, trifluoromethyl, trifluoromethoxy, carboxyl, C1-C4 alkoxy, C1-C4 alkoxy carbonyl, mercapto, C1-C4 acyl and C5-C7 aryl Ar; the aryl or the benzyl is optionally substituted by one or more substituents selected from halogen, C1-C6 linear or branched hydrocarbyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar; the heteroaryl contains 1-3 heteroatoms selected from O, S and N, is optionally combined with phenyl or C5-C7 heteroaryl, or is substituted by one or more substituents selected from halogen, C1-C6 linear or branched hydrocarbyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar;

$R_8$ is selected from H, C1-C6 linear or branched saturated or unsaturated hydrocarbyl, C3-C7 cyclic hydrocarbyl;

$R_9$ and $R_{10}$ are identical or different, and each is independently selected form H,

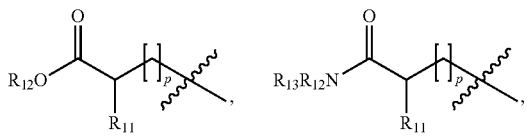

C1-C6 linear or branched saturated or unsaturated hydrocarbyl, C3-C7 cyclic hydrocarbyl, C4-C7 heterocyclic radical, C5-C7 aroylmethylene, 5-7 membered heteroaroylmethylene, benzyl, pyridinedimethylene, C5-C7 aryl Ar or 5-7 membered heteroaryl; wherein the C1-C6 linear or branched saturated or unsaturated hydrocarbyl is optionally substituted by one or more substituents selected from methylsulfonyl, cyclopropyl, hydroxy, C1-C3 alkoxy, C1-C3 alkoxycarbonyl, and epoxypropyl; the heterocyclic radical contains 1-3 heteroatoms selected from O, S and N, the methylene of the heterocyclic radical is optionally substituted by carbonyl or sulfonyl, or the heterocyclic radical is optionally substituted by one or more substituents selected from halogen, C1-C6 linear or branched hydrocarbyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar; the aryl or the benzyl is optionally substituted by one or more substituents selected from halogen, C1-C6 linear or branched hydrocarbyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar; the heteroaryl contains 1-3 heteroatoms selected from O, S and N, is optionally combined with phenyl or C5-C7 heteroaryl, or is substituted by one or more substituents selected from halogen, C1-C6 linear or branched hydrocarbyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar;

P is an integer from 0 to 2;

$R_{11}$, $R_{12}$ and $R_{13}$ are identical or different, each of $R_{11}$, $R_{12}$ and $R_{13}$ is independently selected form H, C1-C6 linear or branched saturated or unsaturated hydrocarbyl, C3-C7 cyclic hydrocarbyl, phenyl or benzyl; wherein the phenyl or benzyl is optionally substituted by one or more substituents selected from halogen, C1-C3 linear or branched hydrocarbyl, cyano, nitro, amino, hydroxy, hydroxymethyl, trifluoromethyl, trifluoromethoxy, carboxyl, and C1-C4 alkoxy;

is 3-7 membered nitrogen-containing heterocyclic radical, wherein the heterocyclic radical further contains 1-3 heteroatoms selected from O, S and N, and the methylene of the heterocyclic radical is optionally substituted by carbonyl or sulfonyl, and the heterocyclic radical is optionally substituted by 1-5 substituents selected from H, C1-C6 linear or branched hydrocarbyl, halogen, cyano, nitro, amino, hydroxy, hydroxymethyl, trifluoromethyl, trifluoromethoxy, carboxyl, an acylamino, carboxylate group, C1-C4 alkoxy carbonyl, mercapto, C1-C4 alkoxy and hydroxamino;

$R_3$ is selected from $NR_{14}R_{15}$ or

wherein $R_{14}$ and $R_{15}$ are identical or different, and each of $R_{14}$ and $R_{15}$ is independently H, C1-C6 linear or branched saturated or unsaturated hydrocarbyl and hydrocarboxyl, C3-C7 cyclic hydrocarbyl, C1-C6 hydrocarbyl amino, C1-C6 hydrocarbyl amino hydroxy, C1-C6 hydrocarbyl amidino, C1-C6 hydrocarbyl guanidyl, benzyl, C5-C7 aryl Ar or 5-7 membered heteroaryl, and the heteroaryl contains 1-3 heteroatoms selected from O, S and N, is optionally combined with phenyl or C5-C7 heteroaryl, or is substituted by one or more substituents selected from halogen, C1-C6 linear or branched hydrocarbyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar;

is 3-7 membered nitrogen-containing heterocyclic radical, and the heterocyclic radical further contains 1-4 heteroatoms selected from O, S and N, and is substituted by 1-5 substituents selected from H, C1-C6 linear or branched hydrocarbyl, halogen, cyano, nitro, amino, hydroxy, hydroxymethyl, trifluoromethyl, trifluoromethoxy, carboxyl, acylamino, carboxylate group, C1-C4 alkoxy carbonyl, mercapto, amidino, guanidyl and hydroxamino;

$R_4$ and $R_5$ are identical or different, and each of $R_4$ and $R_5$ is independently H, halogen, C1-C6 linear or branched hydrocarbyl, cyano, nitro, amino, hydroxy, hydroxymethyl, trifluoromethyl, trifluoromethoxy, carboxyl, C1-C4 alkoxy, mercapto, C1-C4 acyl, C1-C4 sulfonyl, C1-C4 sulfonylamino, aminoacyl or C1-C4 linear or branched alkyl substituted sulfonyl;

the halogen is fluoro, chloro, bromo or iodo.

In another preferred embodiment, $R_1$ and $R_2$ are identical or different and are not hydrogen at the same time, $R_1$ is hydrogen, $CBr_2H$, $CCl_2H$, $CF_2H$, cyano, $CF_3$, aldehyde group, $(CH_2)_mOR_6$, $(CH_2)_mNR_6R_7$,

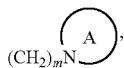

$(CH_2)_mCOOR_8$, $CONR_9R_{10}$ or

$R_2$ is hydrogen, halogen, $CBr_2H$, $CCl_2H$, $CF_2H$, cyano, $CF_3$, aldehyde group, $(CH_2)_mOR_6$, $(CH_2)_mNR_6R_7$,

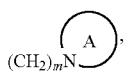

$(CH_2)_mCOOR_8$, $CONR_9R_{10}$ or

or $R_1$ and $R_2$ are optionally linked together to form C3-C6 alkylidene.

In another preferred embodiment, the related disease is selected from the group consisting of non-alcoholic fatty liver, non-alcoholic steatohepatitis and liver fibrosis.

Preferably, in the compound of general formula (I), n is 1;

$R_1$ and $R_2$ are identical or different, and not hydrogen simultaneously, and each of $R_1$ and $R_2$ is independently hydrogen, halogen, $CBr_2H$, $CCl_2H$, $CF_2H$, cyano, $CF_3$, aldehyde group, $(CH_2)_mOR_6$, $(CH_2)_mNR_6R_7$,

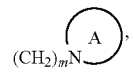

$(CH_2)_mCOOR_8$, $CONR_9R_{10}$, or

wherein, $R_1$ and $R_2$ are optionally linked together to form C3-C6 alkylidene;

m is an integer from 0 to 3;

$R_6$ and $R_7$ are identical or different, and each of $R_6$ and $R_7$ is independently selected from H, C1-C6 linear or branched alkyl, C3-C7 cycloalkyl, C1-C3 alkoxy, 4-7 membered heterocyclic radical, C1-C4 alkyloyl RCO, C5-C7 aryloyl ArCO, C1-C4 alkylsulfonyl $RSO_2$, C5-C7 arylsulfonyl $ArSO_2$, C5-C7 aroylmethylene, 5-7 membered heteroaroylmethylene, benzyl, pyridine dimethylene, C5-C7 aryl Ar or 5-7 membered heteroaryl; wherein, the C1-C6 linear or branched alkyl is optionally substituted by one or more substituents selected from methylsulfonyl, cyclopropyl, hydroxy, C1-C3 alkoxy, C1-C3 alkoxycarbonyl, and epoxypropyl; the heterocyclic radical contains 1-3 heteroatoms selected from O, S and N; the aryl or the benzyl is optionally substituted by one or more substituents selected from halogen, C1-C6 linear or branched alkyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar; the heteroaryl contains 1-3 heteroatoms selected from O, S and N, is optionally combined with phenyl or C5-C7 heteroaryl, or is substituted by one or more substituents selected from halogen, C1-C6 linear or branched hydrocarbyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar;

$R_8$ is selected from hydrogen, C1-C6 linear or branched alkyl;

$R_9$ and $R_{10}$ are identical or different, and each is independently selected form H,

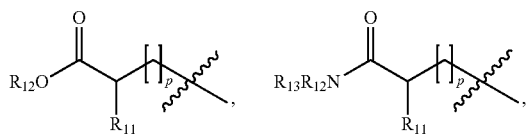

C1-C6 linear or branched alkyl, C3-C7 cycloalkyl, 4-7 membered heterocyclic radical, C5-C7 aroylmethylene, 5-7 membered heteroaroylmethylene, benzyl, pyridinedimethylene, C5-C7 aryl Ar or 5-7 membered heteroaryl; the C1-C6 linear or branched alkyl is optionally substituted by one or more substituents selected from methylsulfonyl, cyclopropyl, hydroxy, C1-C3 alkoxy, C1-C3 alkoxycarbonyl, and epoxypropyl; the heterocyclic radical contains 1-3 heteroatoms selected from O, S and N, the methylene of the heterocyclic radical is optionally substituted by carbonyl or sulfonyl, or the heterocyclic radical is optionally substituted by one or more substituents selected from halogen, C1-C6 linear or branched alkyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar; the aryl or benzyl is optionally substituted by one or more substituents selected from halogen, C1-C6 linear or branched alkyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar; the heteroaryl contains 1-3 heteroatoms selected from O, S and N, is optionally combined with phenyl or C5-C7 heteroaryl, or is substituted by one or more substituents selected from halogen, C1-C6 linear or branched alkyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar;

p is an integer from 0 to 2;

$R_{11}$, $R_{12}$ and $R_{13}$ are identical or different, each of $R_{11}$, $R_{12}$ and $R_{13}$ is independently selected form H, C1-C6 linear or branched alkyl, C3-C7 cycloalkyl, phenyl or benzyl; wherein the phenyl or benzyl is optionally substituted by one or more substituents selected from halogen, C1-C3 linear or branched alkyl, cyano, nitro, amino, hydroxy, hydroxymethyl, trifluoromethyl, trifluoromethoxy, carboxyl, and C1-C4 alkoxy;

is a 3-7 membered nitrogen-containing heterocyclic radical, the heterocyclic radical further contains 1-3 heteroatoms selected from O, S and N, and the methylene of the heterocyclic radical is optionally substituted by carbonyl or sulfonyl, and the heterocyclic radical is optionally substituted by 1-5 substituents selected from H, C1-C6 linear or branched hydrocarbyl, halogen, cyano, nitro, amino, hydroxy, hydroxymethyl, trifluoromethyl, trifluoromethoxy, carboxyl, acylamino, carboxylate group, C1-C4 alkoxy carbonyl, mercapto, C1-C4 alkoxy and hydroxamino;

$R_3$ is selected from $NR_{14}R_{15}$ or

wherein $R_{14}$ and $R_{15}$ are identical or different, and each of $R_{14}$ and $R_{15}$ is independently H, C1-C6 linear or branched alkyl and alkoxy, C3-C7 cycloalkyl, C1-C6 alkylamino, C1-C6 alkyl amino hydroxy, C1-C6 alkyl amidino, C1-C6 alkyl guanidyl, benzyl, C5-C7 aryl Ar or 5-7 membered heteroaryl, and the heteroaryl contains 1-3 heteroatoms selected from O, S and N, is optionally combined with phenyl or C5-C7 heteroaryl, or is substituted by one or more substituents selected from halogen, C1-C6 linear or branched alkyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar;

is a 3-7 membered nitrogen-containing heterocyclic radical, the heterocyclic radical further contains 1-4 heteroatoms selected from O, S and N, and is substituted by 1-5 substituents selected from H, C1-C6 linear or branched alkyl, halogen, cyano, nitro, amino, hydroxy, hydroxymethyl, trifluoromethyl, trifluoromethoxy, carboxyl, acylamino, carboxylate group, C1-C4 alkoxy carbonyl, mercapto, amidino, guanidyl and hydroxamino;

$R_4$ and $R_5$ are identical or different, and each of $R_4$ and $R_5$ is independently H, halogen, C1-C6 linear or branched hydrocarbyl, cyano, nitro, amino, hydroxy, hydroxymethyl, trifluoromethyl, trifluoromethoxy, carboxyl, C1-C4 alkoxy, mercapto, C1-C4 acyl, C1-C4 sulfonyl, C1-C4 sulfonylamino, aminoacyl or C1-C4 linear or branched alkyl substituted sulfonyl;

the halogen is fluoro, chloro, bromo or iodo.

More preferably, in the compound of general formula (I), n is 1;

$R_1$ and $R_2$ are identical or different, and not hydrogen simultaneously, and each of $R_1$ and $R_2$ is independently H, halogen, $CBr_2H$, $CCl_2H$, $CF_2H$, cyano, $CF_3$, aldehyde group, $(CH_2)_mOR_6$, $(CH_2)_mNR_6R_7$,

$(CH_2)_mCOOR_8$, $CONR_9R_{10}$,

wherein, $R_1$ and $R_2$ are optionally linked together to form C3-C6 alkylidene;

m is an integer from 0 to 3;

$R_6$ and $R_7$ are identical or different, and each of $R_6$ and R is independently selected from H, C1-C6 linear or branched alkyl, C3-C7 cycloalkyl, C1-C3 alkoxy, 4-7 membered heterocyclic radical, C1-C4 alkyloyl RCO, C5-C7 aryloyl ArCO, C1-C4 alkylsulfonyl $RSO_2$, C5-C7 arylsulfonyl $ArSO_2$, C5-C7 aroylmethylene, 5-7 membered heteroaroylmethylene, benzyl, pyridine dimethylene, C5-C7 aryl Ar or 5-7 membered heteroaryl; wherein, the linear or branched C1-C6 alkyl is optionally substituted by one or more substituents selected from methylsulfonyl, cyclopropyl, hydroxy, C1-C3 alkoxy, C1-C3 alkoxycarbonyl, and epoxypropyl; the heterocyclic radical contains 1-3 heteroatoms selected from O, S and N; the aryl or the benzyl is optionally substituted by one or more substituents selected from halogen, C1-C6 linear or branched alkyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar; the heteroaryl contains 1-3 heteroatoms selected from O, S and N, is optionally combined with phenyl or C5-C7 heteroaryl, or is substituted by one or more substituents selected from halogen, C1-C6 linear or branched hydrocarbyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar;

$R_8$ is selected from hydrogen, C1-C6 linear or branched alkyl;

$R_9$ and $R_{10}$ are identical or different, and each is independently selected form H,

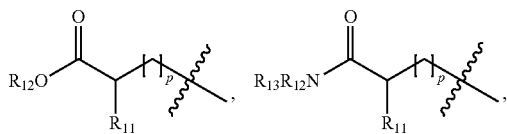

C1-C6 linear or branched alkyl, C3-C7 cycloalkyl, 4-7 membered heterocyclic radical, C5-C7 aroylmethylene, 5-7 membered heteroaroylmethylene, benzyl, pyridinedimethylene, C5-C7 aryl Ar or 5-7 membered heteroaryl; the C1-C6 linear or branched alkyl is optionally substituted by one or more substituents selected from methylsulfonyl, cyclopropyl, hydroxy, C1-C3 alkoxy, C1-C3 alkoxycarbonyl, and epoxypropyl; the heterocyclic radical contains 1-3 heteroatoms selected from O, S and N, the methylene of the heterocyclic radical is optionally substituted by carbonyl or sulfonyl, or the heterocyclic radical is optionally substituted by one or more substituents selected from halogen, C1-C6 linear or branched alkyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar; the aryl or benzyl can be substituted by one or more substituents selected from halogen, C1-C6 linear or branched alkyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar; the heteroaryl contains 1-3 heteroatoms selected from O, S and N, is optionally combined with phenyl or C5-C7 heteroaryl, or is substituted by one or more substituents selected from halogen, C1-C6 linear or branched alkyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar;

p is an integer from 0 to 2;

$R_{11}$, $R_{12}$ and $R_{13}$ are identical or different, each of $R_{11}$, $R_{12}$ and $R_{13}$ is independently selected form H, C1-C6 linear or branched alkyl, C3-C7 cycloalkyl, phenyl or benzyl; wherein the phenyl or benzyl is optionally substituted by one or more substituents selected from halogen, C1-C3 linear or branched alkyl, cyano, nitro, amino, hydroxy, hydroxymethyl, trifluoromethyl, trifluoromethoxy, carboxyl, and C1-C4 alkoxy;

is a 3-7 membered nitrogen-containing heterocyclic radical, the heterocyclic radical further contains 1-3 heteroatoms selected from O, S and N, and the methylene of the heterocyclic radical is optionally substituted by carbonyl or sulfonyl, and the heterocyclic radical is optionally substituted by 1-5 substituents selected from H, C1-C6 linear or branched hydrocarbyl, halogen, cyano, nitro, amino, hydroxy, hydroxymethyl, trifluoromethyl, trifluoromethoxy, carboxyl, acylamino, carboxylate group, C1-C4 alkoxy carbonyl, mercapto, C1-C4 alkoxy and hydroxamino;

$R_3$ is selected from $NR_{14}R_{15}$ or

wherein $R_{14}$ and $R_{15}$ are identical or different, and each of $R_{14}$ and $R_{15}$ is independently H, C1-C6 linear or branched alkyl and alkoxy, C3-C7 cycloalkyl, C1-C6 alkylamino, C1-C6 alkyl amino hydroxy, C1-C6 alkyl amidino, C1-C6 alkyl guanidyl, benzyl, C5-C7 aryl Ar or 5-7 membered heteroaryl, and the heteroaryl contains 1-3 heteroatoms selected from O, S and N, is optionally combined with phenyl or C5-C7 heteroaryl, or is substituted by one or more substituents selected from halogen, C1-C6 linear or branched alkyl, cyano, nitro, amino, hydroxy, hydroxymethyl, trifluoromethyl, trifluoromethoxy, carboxyl, C1-C4 alkoxy, mercapto, C1-C4 acyl and C5-C7 aryl Ar;

is a 3-7 membered nitrogen-containing heterocyclic radical, the heterocyclic radical further contains 1-4 heteroatoms selected from O, S and N, and is substituted by 1-5 substituents selected from H, C1-C6 linear or branched alkyl, halogen, cyano, nitro, amino, hydroxy, hydroxymethyl, trifluoromethyl, trifluoromethoxy, carboxyl, acylamino, carboxylate group, C1-C4 alkoxy carbonyl, mercapto, amidino, guanidyl and hydroxamino;

$R_4$ and $R_5$ are identical or different, and each of $R_4$ and $R_5$ is independently H, halogen, C1-C6 linear or branched hydrocarbyl, cyano, nitro, amino, hydroxy, hydroxymethyl, trifluoromethyl, trifluoromethoxy, carboxyl, C1-C4 alkoxy, mercapto, C1-C4 acyl, C1-C4 sulfonyl, C1-C4 sulfonyl amino, aminoacyl or C1-C4 linear or branched alkyl substituted sulfonyl;

the halogen is fluoro, chloro, bromo or iodo.

Further preferably, in the compound of general formula (I), n=1, $R_1$ and $R_2$ are identical or different, and not hydrogen simultaneously, and each of $R_1$ and $R_2$ is independently H, halogen, $(CH_2)_m COOR_8$, $CONR_9R_{10}$,

wherein, m is an integer from 0 to 3;

$R_8$ is selected from hydrogen or C1-C3 linear or branched alkyl;

$R_9$ and $R_{10}$ are identical or different, and each is independently selected form H, C1-C3 linear or branched alkyl, C3-C6 cycloalkyl, C4-C6 heterocyclyl, phenyl or 5-7 membered heteroaryl; wherein, the C1-C3 linear or branched alkyl is optionally substituted by C1-C3 alkoxycarbonyl; the heterocyclyl contains one heteroatom selected from O, S and N; the heteroaryl contains one heteroatom selected from O, S and N;

is pyrrolidinyl, piperidinyl, morpholinyl, piperazinyl, homopiperazinyl or thiomorpholinyl, and is optionally substituted by 1 to 2 substituents selected from H, C1-C3 linear or branched alkyl, halogen, hydroxyl and C1-C4 alkoxycarbonyl;

R₃ is pyrrolidinyl, piperidinyl, morpholinyl, piperazinyl, homopiperazinyl or thiomorpholinyl, and is substituted by cyano, amino or hydroxy;

R₄ and R₅ are identical or different, and each of R₄ and R₅ is independently H, fluorine, chlorine, bromine, methyl, ethyl, cyano or hydroxyl.

The most preferred thieno[3,2-d]pyrimidin-4-one compounds in the present invention and pharmaceutically acceptable salts, solvates, stereoisomers, tautomers, and prodrugs thereof are selected from the following compounds:

| No. | Structure |
|---|---|
| DC291407 | 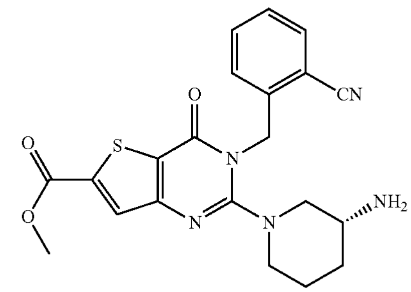 [SMILES: COC(=O)c1cc2nc(N3CCC[C@@H](N)C3)n(Cc3ccccc3C#N)c(=O)c2s1] |
| DC291410 | 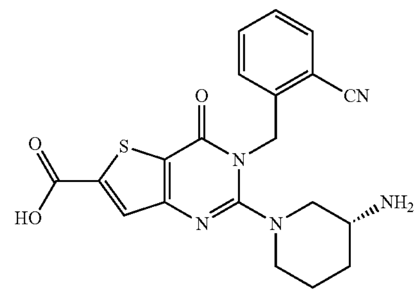 [SMILES: N#Cc1ccccc1Cn1c(N2CCC[C@@H](N)C2)nc2cc(C(=O)O)sc2c1=O] |
| DC291419 | 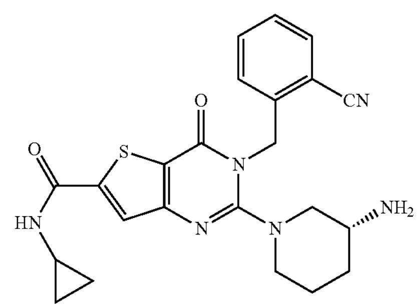 [SMILES: N#Cc1ccccc1Cn1c(N2CCC[C@@H](N)C2)nc2cc(C(=O)NC3CC3)sc2c1=O] |
| DC291416 | 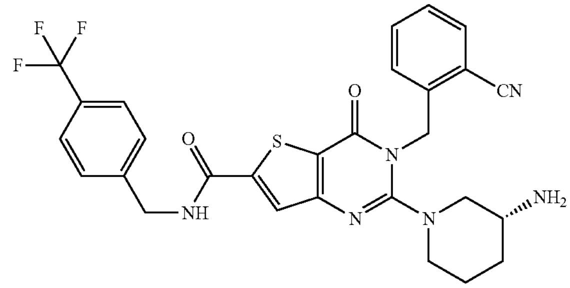 [SMILES: N#Cc1ccccc1Cn1c(N2CCC[C@@H](N)C2)nc2cc(C(=O)NCc3ccc(C(F)(F)F)cc3)sc2c1=O] |

| No. | Structure |
|---|---|
| DC291417 | 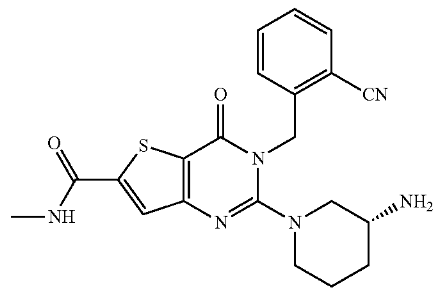 [SMILES: CNC(=O)c1cc2nc(N3CCC[C@@H](N)C3)n(Cc3ccccc3C#N)c(=O)c2s1] |
| DC291002 | 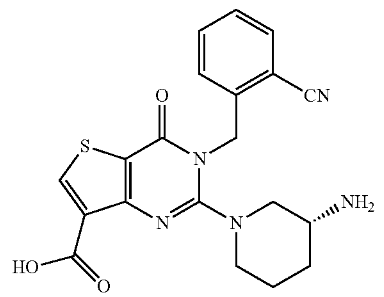 [SMILES: N#Cc1ccccc1Cn1c(N2CCC[C@@H](N)C2)nc2c(C(=O)O)csc2c1=O] |
| DC291011 | 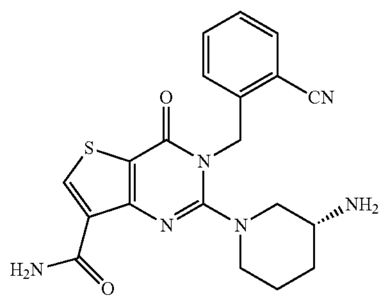 [SMILES: N#Cc1ccccc1Cn1c(N2CCC[C@@H](N)C2)nc2c(C(N)=O)csc2c1=O] |
| DC291418 | 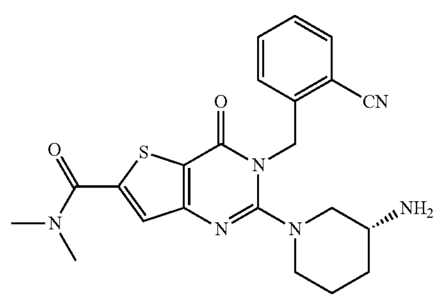 [SMILES: CN(C)C(=O)c1cc2nc(N3CCC[C@@H](N)C3)n(Cc3ccccc3C#N)c(=O)c2s1] |
| DC291420 | 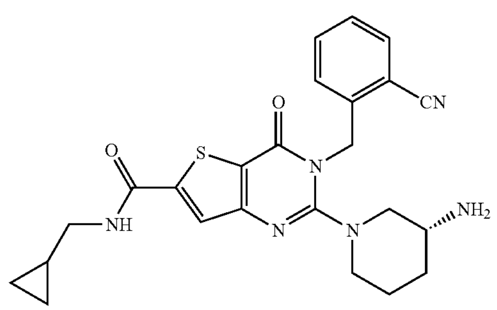 [SMILES: N#Cc1ccccc1Cn1c(N2CCC[C@@H](N)C2)nc2cc(C(=O)NCC3CC3)sc2c1=O] |

| No. | Structure |
|---|---|
| DC291409 | 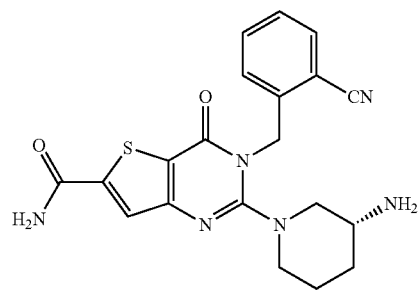 [SMILES: N#Cc1ccccc1Cn1c(N2CCC[C@@H](N)C2)nc2cc(C(N)=O)sc2c1=O] |
| DC291423 | 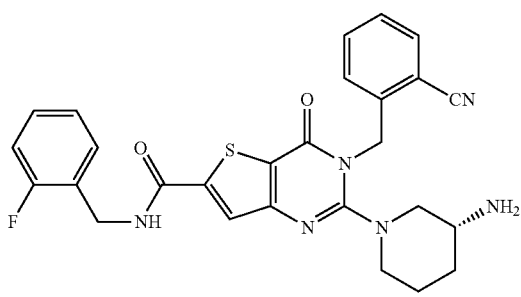 [SMILES: N#Cc1ccccc1Cn1c(N2CCC[C@@H](N)C2)nc2cc(C(=O)NCc3ccccc3F)sc2c1=O] |
| DC291009 | 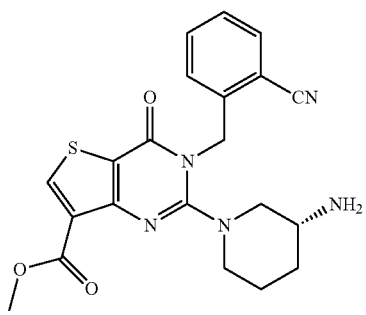 [SMILES: COC(=O)c1csc2c(=O)n(Cc3ccccc3C#N)c(N3CCC[C@@H](N)C3)nc12] |
| DC291010 | 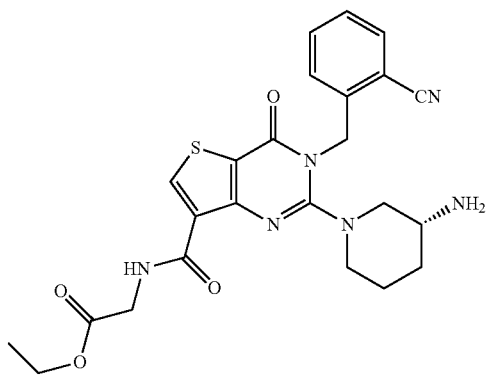 [SMILES: CCOC(=O)CNC(=O)c1csc2c(=O)n(Cc3ccccc3C#N)c(N3CCC[C@@H](N)C3)nc12] |

-continued

| No. | Structure |
|---|---|
| DC291012 | 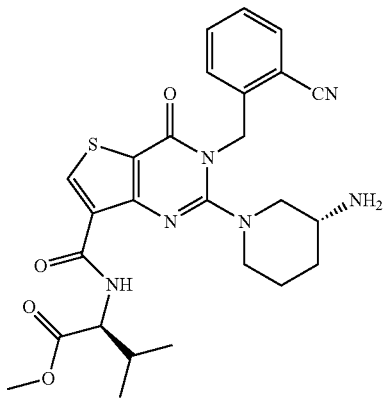 [SMILES: COC(=O)[C@@H](NC(=O)c1csc2c(=O)n(Cc3ccccc3C#N)c(N3CCC[C@@H](N)C3)nc12)C(C)C] |
| DC291013 | 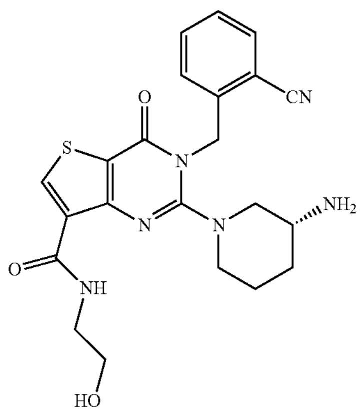 [SMILES: N#Cc1ccccc1Cn1c(N2CCC[C@@H](N)C2)nc2c(C(=O)NCCO)csc2c1=O] |
| DC291014 | 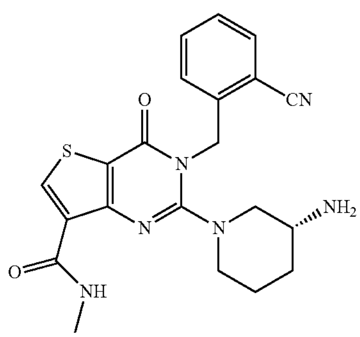 [SMILES: CNC(=O)c1csc2c(=O)n(Cc3ccccc3C#N)c(N3CCC[C@@H](N)C3)nc12] |
| DC291015 | 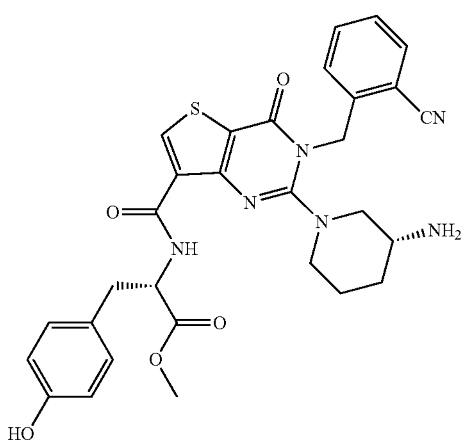 [SMILES: COC(=O)[C@H](Cc1ccc(O)cc1)NC(=O)c1csc2c(=O)n(Cc3ccccc3C#N)c(N3CCC[C@@H](N)C3)nc12] |

| No. | Structure |
|---|---|
| DC291016 | 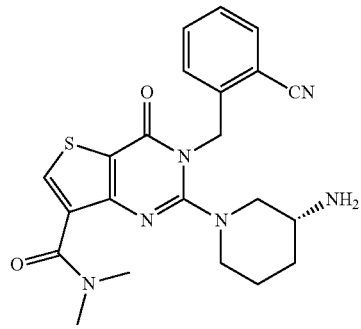 [SMILES: CN(C)C(=O)c1csc2c(=O)n(Cc3ccccc3C#N)c(N3CCC[C@@H](N)C3)nc12] |
| DC291017 | 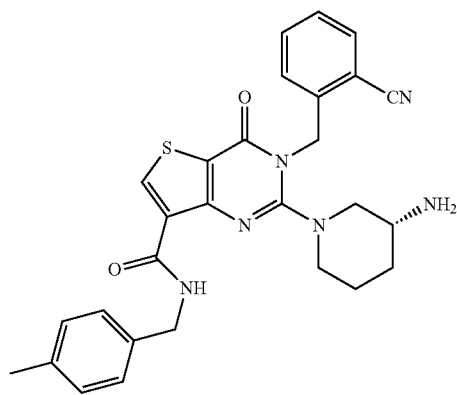 [SMILES: Cc1ccc(CNC(=O)c2csc3c(=O)n(Cc4ccccc4C#N)c(N4CCC[C@@H](N)C4)nc23)cc1] |
| DC291018 | 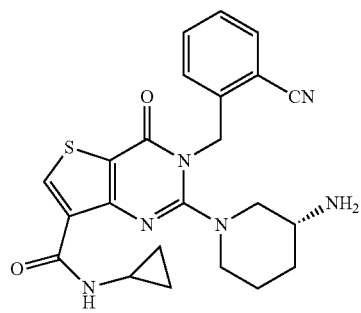 [SMILES: N#Cc1ccccc1Cn1c(N2CCC[C@@H](N)C2)nc2c(C(=O)NC3CC3)csc2c1=O] |
| DC291022 | 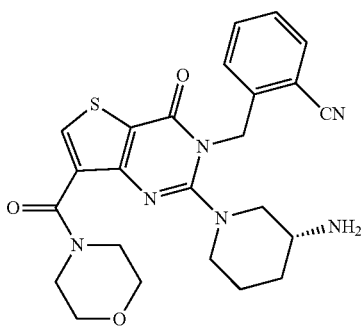 [SMILES: N#Cc1ccccc1Cn1c(N2CCC[C@@H](N)C2)nc2c(C(=O)N3CCOCC3)csc2c1=O] |

| No. | Structure |
| --- | --- |
| DC291023 | 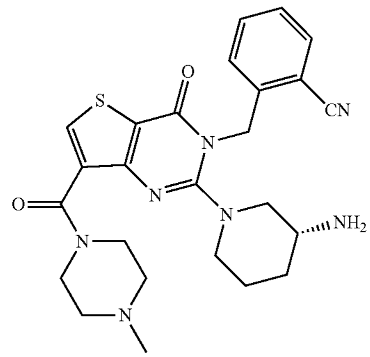 [SMILES: CN1CCN(C(=O)c2csc3c(=O)n(Cc4ccccc4C#N)c(N4CCC[C@@H](N)C4)nc23)CC1] |

The most preferred compound in the present invention is (R)-methyl-2-(3-aminopiperidin-1-yl)-3-(2-cyanobenzyl)-4-carbonyl-3,4-dihydrothieno[3,2-d]pyrimidine-6 carboxylic acid (DC291407), and pharmaceutically acceptable salts, solvates, stereoisomers, and tautomers thereof.

Another preferred compound in the present invention is (R)-2-(3-aminopiperidin-1-yl)-3-(2-cyanobenzyl)-4-carbonyl-3,4-dihydrothieno[3,2-d]pyrimidine-6 carboxylic acid (DC291410), and pharmaceutically acceptable salts, solvates, stereoisomers, and tautomers thereof.

The pharmaceutically acceptable salts include conventional pharmaceutically acceptable salts formed by the reaction of the compounds of the present invention with inorganic or organic acids. For example, conventional pharmaceutically acceptable salts can be prepared by reacting the compounds of the present invention with inorganic or organic acids, wherein the inorganic acids include hydrochloric acid, hydrobromic acid, sulfuric acid, nitric acid, aminosulfonic acid, phosphoric acid, etc., and the organic acids include citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalene disulfonic acid, maleic acid, malic acid, malonic acid, fumaric acid, succinic acid, propionic acid, oxalic acid, trifluoroacetic acid, stearic acid, pamoic acid, hydroxylmaleic acid, phenylacetic acid, benzoic acid, salicylic acid, glutamic acid, ascorbic acid, p-aminobenzenesulfonic acid, 2-acetoxybenzoic acid, isethionic acid, etc. Alternatively, the salts are sodium, potassium, calcium, aluminum or ammonium salts formed by the compound of the present invention and an inorganic base; or methylamine, ethylamine or ethanolamine salts formed by the compound of the present invention and an organic base.

Another object of the present invention is to provide a pharmaceutical composition comprising a therapeutically effective amount of thieno[3,2-d]pyrimidin-4-one compound represented by the following general formula (I), pharmaceutically acceptable salt, solvate, stereoisomer, tautomer or prodrug thereof; and a pharmaceutically acceptable carrier. "Pharmaceutically acceptable carrier" refers to one or more compatible solid or liquid fillers or gel substances, which are suitable for human use, and must have sufficient purity and sufficiently low toxicity. "Compatibility" herein means that each component of the composition can be blended with the compound of general formula I of the present invention, the pharmaceutically acceptable salt or solvate thereof and mixture thereof, without significantly reducing the efficacy of the active ingredient. Examples of pharmaceutically acceptable carriers include cellulose and its derivatives (such as sodium carboxymethyl cellulose, sodium ethyl cellulose, cellulose acetate, etc.), gelatin, talc, and solid lubricants (such as stearic acid, magnesium stearate), calcium sulfate, vegetable oils (such as soybean oil, sesame oil, peanut oil, olive oil, etc.), polyols (such as propylene glycol, glycerin, mannitol, sorbitol, etc.), emulsifiers (such as Tween®), wetting agents (such as sodium lauryl sulfate), coloring agents, flavoring agents, stabilizers, antioxidants, preservatives, pyrogen-free water, etc.

The present invention relates to a medicament for the treatment and/or prevention of non-alcoholic fatty liver, non-alcoholic steatohepatitis and liver fibrosis prepared by using the thieno[3,2-d]pyrimidin-4-one compound represented by the general formula (I), pharmaceutically acceptable salt, solvate, stereoisomer, tautomer or prodrug thereof and mixture thereof as active ingredient.

The medicament can be introduced into the body such as muscle, intradermal, subcutaneous, vein, mucosal tissue by injection, spray, nose drops, eye drops, penetration, absorption, physically or chemically mediated methods; or it can be mixed or packaged by other substances and introduced into the body.

When needed, one or more pharmaceutically acceptable carriers can be added to the above-mentioned medicament. The carrier includes pharmaceutically conventional diluents, excipients, fillers, binders, wetting agents, disintegrants, absorption promoters, surfactants, adsorption carriers, lubricants and the like.

The thieno[3,2-d]pyrimidin-4-one compound represented by the general formula (I), pharmaceutically acceptable salt, ester, solvate, stereoisomer, tautomer or prodrug thereof as active ingredient can be formulated alone or in combination with other medicaments, adjuvants, etc. so as to produce various dosage forms, including but not limited to tablet, powder, pill, injection, capsule, film, suppositorie, ointment, electuary and other forms. The above-mentioned various dosage forms of medicaments can be prepared according to conventional methods in the pharmaceutical field.

The present invention also provides a method for treating and/or preventing liver fibrosis and related diseases by administering the above-mentioned thieno[3,2-d]pyrimidin-4-one compound represented by the general formula (I), the pharmaceutically acceptable salt, solvate, stereoisomer, or tautomer thereof to a subject in need thereof.

The present invention also provides a method for inhibiting DPP-4 by administering the above-mentioned thieno [3,2-d]pyrimidin-4-one compound represented by the general formula (I), the pharmaceutically acceptable salt, solvate, stereoisomer, or tautomer thereof to a subject in need thereof.

It should be understood that within the scope of the present invention, the above-mentioned each technical feature of the present invention and each technical features specifically described in the following (such as the examples) can be combined with each other to form a new or preferred technical solution. Each feature disclosed in the specification can be replaced by any alternative feature that provides the same, equal or similar purpose. Due to space limitations, it won't be repeated herein.

DETAILED DESCRIPTION

Figure 1:
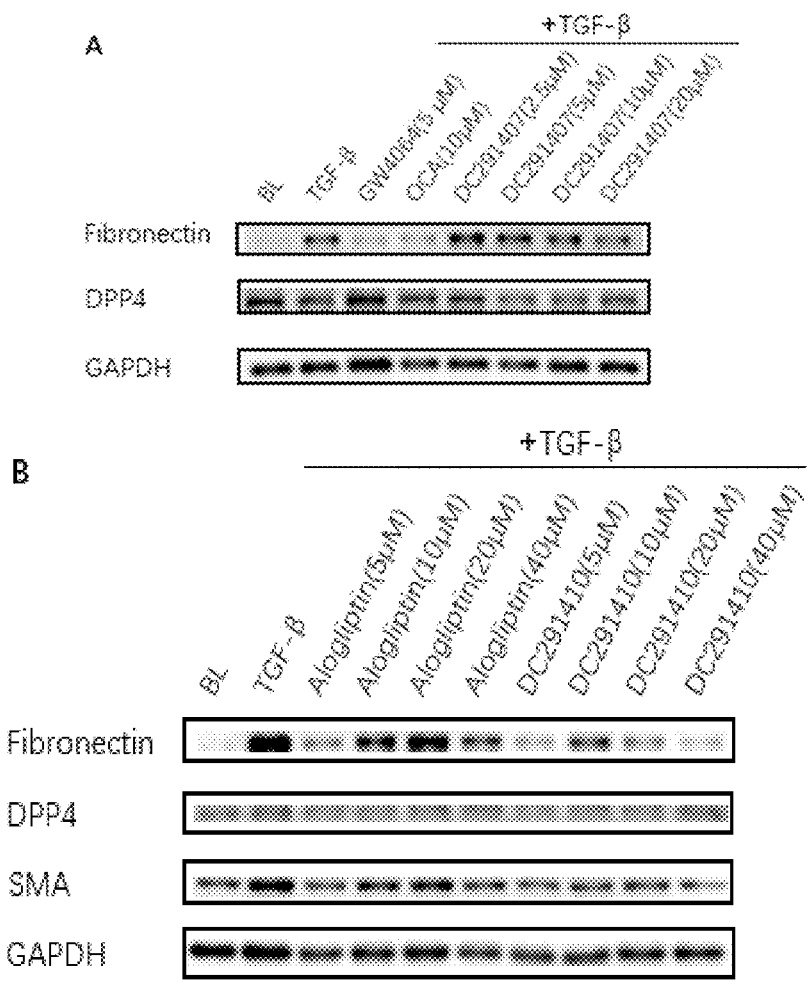
FIG. 1 shows the results of the DPP-4 inhibitor in Example 3 of the present invention on inhibiting hepatic stellate cell activation.

The inventors of the present application have conducted extensive and intensive research and have found that thieno [3,2-d]pyrimidin-4-one compounds can improve liver function, down-regulate the expression of α-SMA and Col1α1 mRNA, and reduce the deposition of collagen in the liver, and can be used to treat and/or prevent liver fibrosis and related diseases. On this basis, the present invention has been completed.

Terms

"Alkyl" refers to a straight-chain or branched saturated aliphatic hydrocarbon group, for example, "$C_{1-8}$ alkyl" refers to a straight-chain and branched alkyl group including 1 to 8 carbon atoms, including but not limited to methyl, ethyl, n-propyl, isopropyl, n-butyl, isobutyl, tert-butyl, sec-butyl, n-pentyl, etc.

"Cyclic hydrocarbyl" refers to a saturated or partially unsaturated monocyclic or polycyclic cyclic hydrocarbon substituent. For example, "$C_{3-8}$ cycloalkyl" refers to a cycloalkyl group containing 3 to 8 carbon atoms, which is classified as monocyclic cycloalkyl, and polycyclic cycloalkyl, wherein monocyclic cycloalkyl includes but not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. Polycyclic cycloalkyl includes spiro, fused, and bridged cycloalkyls.

"Heterocyclic radical (or heterocyclyl)" refers to a saturated or partially unsaturated monocyclic or polycyclic cyclic hydrocarbon substituent in which one or more ring atoms are selected from N, O or S.

"Aryl" refers to an all-carbon monocyclic or fused polycyclic group (that is, a ring that shares adjacent pairs of carbon atoms), a polycyclic ring with a conjugated π-electron system (that is, a ring with adjacent pairs of carbon atoms), including but not limited to phenyl and naphthyl.

"Heteroaryl" refers to a heteroaromatic system containing 1 to 4 heteroatoms including N, O and S, for example, a 5-7 membered heteroaryl refers to a heteroaromatic system containing 5-7 ring atoms, 5-10 membered heteroaryl refers to heteroaromatic system containing 5-10 ring atoms, including but not limited to furyl, thienyl, pyridyl, pyrrolyl, N-alkylpyrrolyl, pyrimidinyl, pyrazinyl, imidazolyl, tetrazolyl, etc.

"Alkoxy" refers to —O-(alkyl), where the definition of alkyl is as described above. For example, "$C_{1-8}$ alkoxy" refers to an alkyloxy group containing 1-8 carbons, including but not limited to methoxy, ethoxy, propoxy, butoxy, etc.

The present invention will be further described below in conjunction with specific examples. It should be understood that these examples are only used to illustrate the present invention and not to limit the scope of the present invention. The experimental methods that do not indicate specific conditions in the following examples usually follow conventional conditions (such as the conditions described in Sambrook et al., Molecular Cloning: Laboratory Manual (New York: Cold Spring Harbor Laboratory Press, 1989)) or according to the conditions suggested by the manufacturer. Unless otherwise specified, percentages and parts are percentages by weight and parts by weight.

Unless otherwise defined, all professional and scientific terms used herein have the same meanings as those familiar to those skilled in the art. In addition, any methods and materials similar or equivalent to the contents described can be applied to the method of the present invention. The preferred embodiments and materials described herein are for demonstration purpose only.

Example 1 Preparation of DC291407

Synthetic Route:

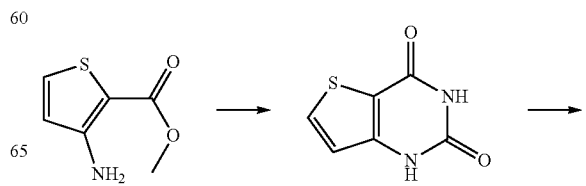

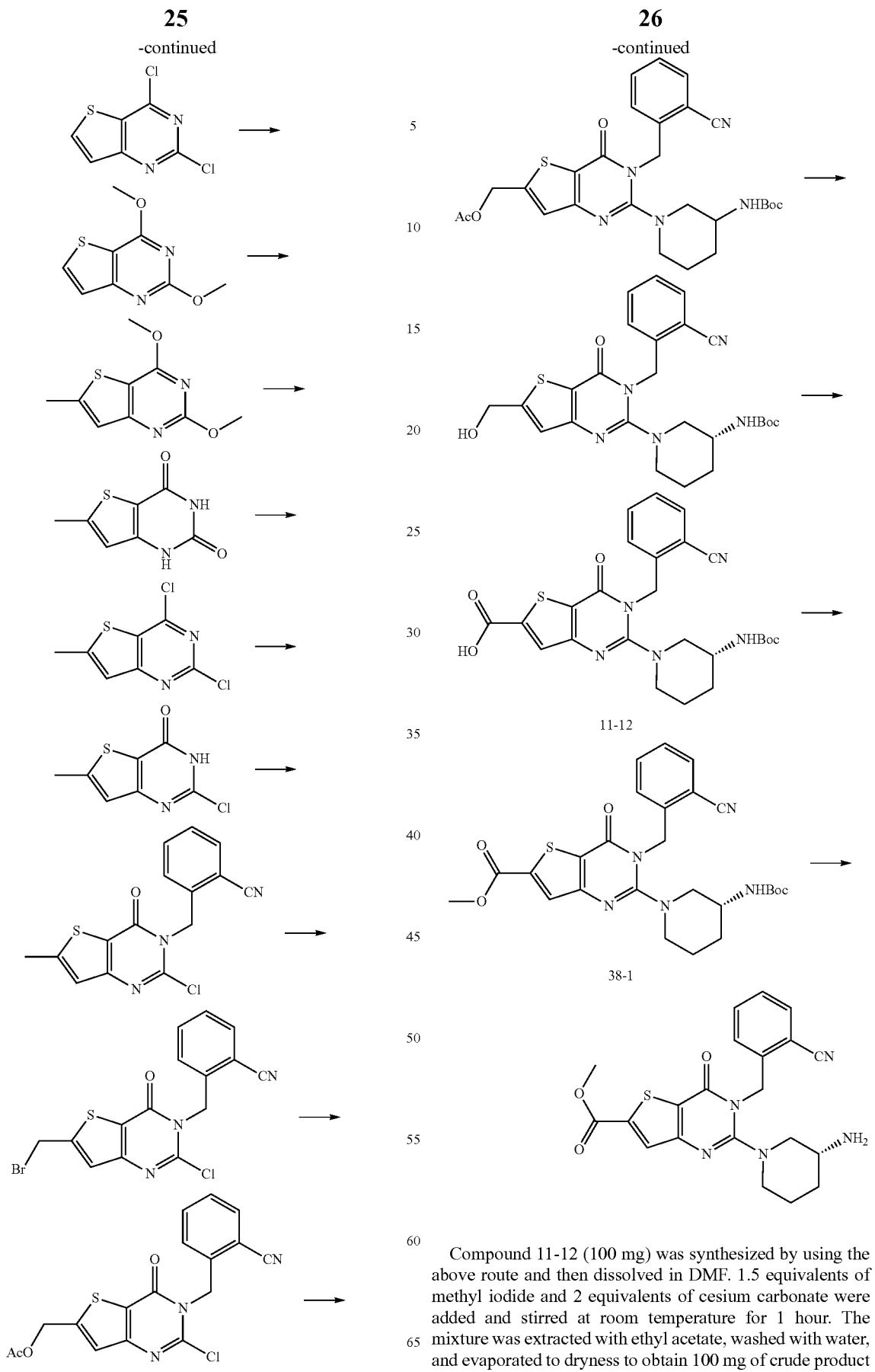
Compound 11-12 (100 mg) was synthesized by using the above route and then dissolved in DMF. 1.5 equivalents of methyl iodide and 2 equivalents of cesium carbonate were added and stirred at room temperature for 1 hour. The mixture was extracted with ethyl acetate, washed with water, and evaporated to dryness to obtain 100 mg of crude product 38-1.

Compound 38-1 was dissolved in 40 ml of DCM and 15 ml TFA was added and stirred at room temperature for 4 hours. The solvent was removed by rotary evaporation and the residue was dissolved in 50 ml ethyl acetate, washed with saturated potassium carbonate solution and then saturated sodium chloride solution. The solvent was removed by rotary evaporation and the residue was separated by column chromatography (DCM: CH$_3$OH=5:1) to obtain compound DC291407.

$^1$H-NMR (CDCl$_3$-d$_3$): δ=7.761(s, 1H), 7.610(d, 1H), 7.493(t, 1H), 7.320(t, 1H), 7180(d, 1H), 5.500(quartet, 2H), 3.895(s, 3H), 3.680(d,2H), 3.355(m, 1H), 3.010(m, 2H), 2.150(m, 1H), 1.894(m,2H), 1.644(m, 1H); LC-MS m/z 424.1 [M+H]$^+$.

Example 2 Preparation of DC291410

Synthetic Route:

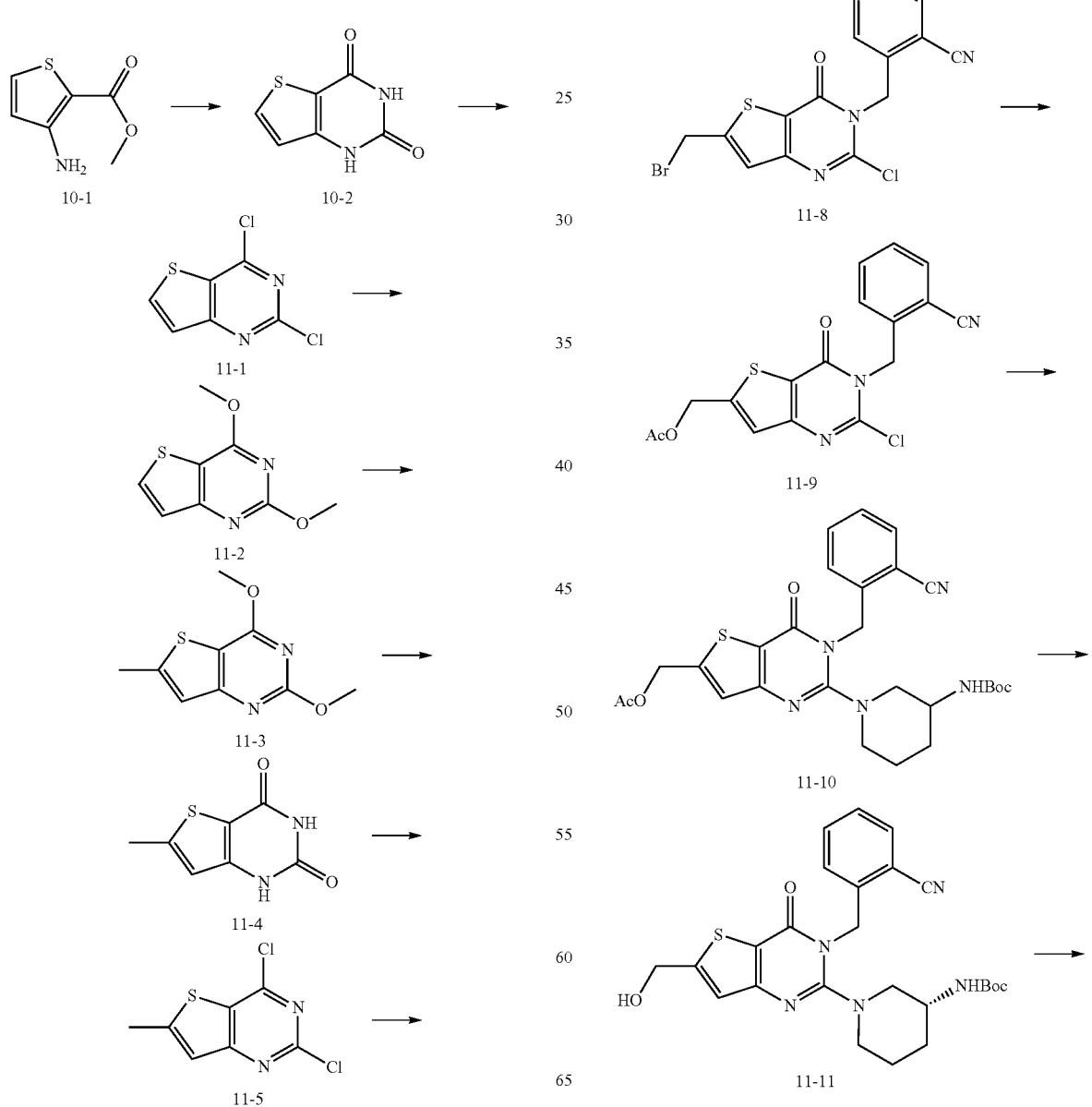

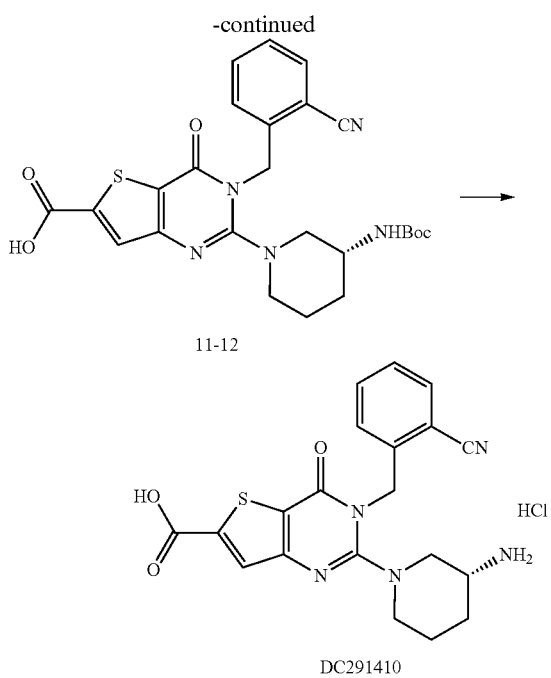

Compound 11-12 (100 mg, 0.237 mmol) was dissolved in 20 ml of ether hydrochloride, stirred at room temperature for 1 hour, and evaporated to dryness to obtain compound DC291410 (70 mg) with a yield of 80%, MS: 410.1 $[M+H]^+$.

Example 3 Treatment of Liver Fibrosis with DPP-4 Inhibitor

Human hepatic stellate cell line LX-2 was used in cell function experiments. The hepatic stellate cell activation and inducement agent TGF-β was added to activate hepatic stellate cells thereby significantly increasing the expression of multiple extracellular matrixes. By comparing the expression levels of extracellular matrix in the TGF-β group and the cell group in which TGF-β and the compound to be tested were both added at the same time, the efficacy of the compound in alleviating liver fibrosis through hepatic stellate cells was characterized.

The cell experiment procedure was as follows. The human hepatic stellate cell line LX-2 was selected and inoculated into the treated 24-well plate at $7.5 \times 10^4$/well. After the cells were adhered overnight and they were subjected to starvation treatment for 12 hours, the cells were treated with 10 ng/mL TGF-β and the corresponding test compound for 24 hours and then protein samples were collected. The expression of extracellular matrix represented by α-smooth muscle myofilament (α-SMA) and fibronectin was detected by Western Blot.

The compounds of the present invention were all high-activity inhibitors of DPP-4, among which two compounds, DC291407 and DC291410 concentration-dependently inhibited the activation of hepatic stellate cells HSC as the concentration increased, and the inhibitory activity was better than that of the positive control Alogliptin, as shown in FIG. 1. Such compounds have good application prospects in the treatment of liver fibrosis, and therefore have good commercial value.

The efficacy of DC291407 was investigated in the cell function test, and it was found that it had an inhibitory effect on the activation of HSC (OCA (obeticholic acid) and GW4064 were used as positive controls). Subsequently, the inhibitory effect of DC291410, a metabolite of DC291407 on the activation of hepatic stellate cells, was evaluated on this cell system. The results showed that the inhibitory activity of DC291410 on HSC activation was better than that of the positive control Alogliptin.

Example 4 Test of In Vivo Pharmacological Activity on Liver Fibrosis

In this experiment, $CCl_4$ induced liver fibrosis model mice were used to investigate the effect of long-term oral administration of compound DC291407 on liver fibrosis in the model mice.

Animal experiment: Male C57BL/6j mice were injected intraperitoneally with 2 mL/kg, 10% $CCl_4$ (dissolved in olive oil) three times a week to induce liver fibrosis model. Two weeks after modeling, the blood was taken from the retro-ocular venous plexus of the mice, and serum ALT and AST indexes were detected. According to ALT, AST, body weight and other indexes, the mice were randomly divided into 5 groups, each with 10 mice. There were the model control group (vehicle), DC291407 low-dose group (20 mg/kg), DC291407 high-dose group (60 mg/kg), positive compound OCA low-dose group (20 mg/kg), OCA high-dose group (40 mg/kg), respectively, and mice were administered by oral gavage. DC291407 was administered twice a day, and the other groups were administered once a day. During the administration period, the animals' food intake and body weight were monitored. After 3 weeks of administration, the blood was taken from the retro-ocular venous plexus of the mice, and serum ALT and AST indexes were detected. After 6 weeks of administration, the blood was taken from the retro-ocular venous plexus of the mice and then the mice were killed by dislocation. The liver was taken and weighed, part of the liver was fixed with 4% paraformaldehyde, and part of the liver was frozen at −80° C. During the whole experiment, another 10 mice in the same cage were injected intraperitoneally with the same dose of olive oil as a normal control group (WT). This experiment reflected whether the compound had the effect of relieving liver fibrosis by detecting the levels of liver function indexes ALT and AST in serum, the expression of α-SMA and Col1α1 gene levels in the liver, the content of hydroxyproline (a characteristic amino acid of collagen) in the liver, and liver pathological changes (Sirius scarlet staining) and the like.

Figure 2:
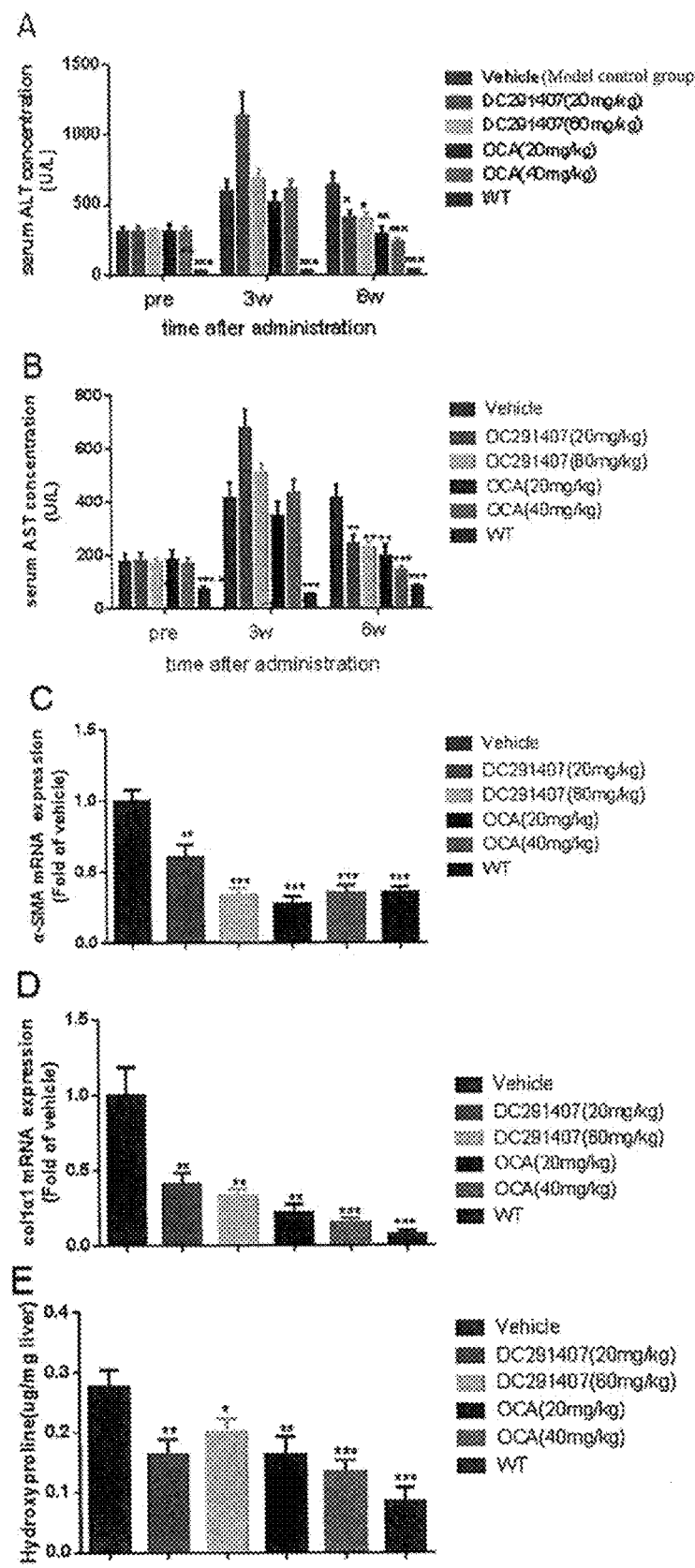
FIG. 2 shows the results of the DPP-4 inhibitor in Example 4 of the present invention on alleviating liver injury blood biochemical indexes, liver fibrosis-related gene expression and collagen characteristic amino acid indexes in $CCl_4$-induced liver fibrosis model mice, wherein the bars from the left to the right represent model control group, DC291407 (20 mg/kg), DC291407 (60 mg/kg), OCA (20 mg/kg), OCA (40 mg/kg), WT, respectively.
Figure 3:
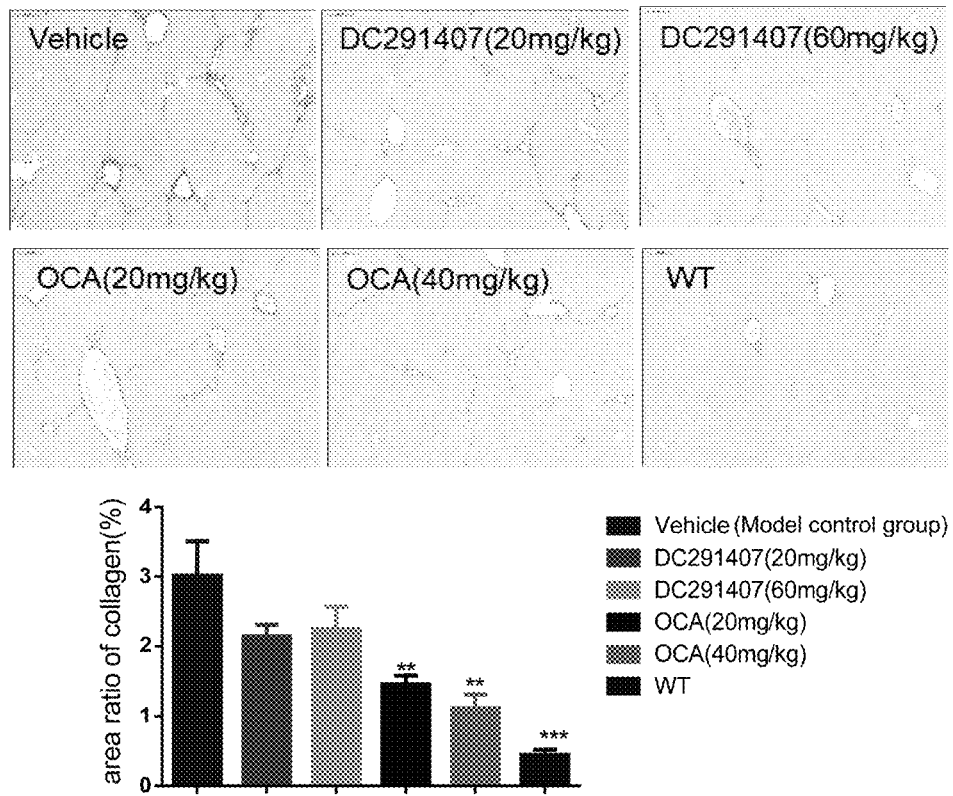
FIG. 3 shows the results of the DPP-4 inhibitor in Example 4 of the present invention on alleviating the pathological indexes of collagen deposition in liver pathological sections in $CCl_4$-induced liver fibrosis model mice, wherein the bars from the left to the right represent model control group, DC291407 (20 mg/kg), DC291407 (60 mg/kg), OCA (20 mg/kg), OCA (40 mg/kg), WT, respectively.

The results of the study showed that no decrease in serum ALT and AST levels was observed after 3 weeks of administration of Compound DC291407 of the present invention, and the level of ALT and AST in the serum could be significantly reduced after 6 weeks of administration; the expression of α-SMA and Col1α1 mRNA in liver tissues was significantly down-regulated after 6 weeks of administration and the content of hydroxyproline in liver tissues was reduced (FIG. 2). In the quantitative analysis of liver pathological sections stained with Sirius scarlet, the test compound DC291407 could reduce the collagen content in the liver without statistical difference (FIG. 3).

In summary, long-term administration of the test compound DC291407 significantly improved the liver function in $CCl_4$-induced liver fibrosis mice, down-regulated the expression of α-SMA and Col1α1 mRNA, reduced the deposition of collagen in the liver, and had a certain alleviating effect on liver fibrosis.

Example 5 Test of In Vivo Pharmacological Activity on Liver Fibrosis

In this experiment, the NAFLD model of ob/ob mice induced by high-fat diet was used to investigate the treatment effect of long-term oral administration of compound DC291407 on NAFLD.

Animal experiment: ob/ob obese mice were divided into 3 groups according to random blood glucose, random body weight, fasting blood glucose, and fasting body weight at the 8th week of age, with 9 mice in each group. There were the model control group (vehicle) and the DC291407 group (20 mg/kg), the positive compound Alogliptin group (20 mg/kg), respectively and mice were administered by oral gavage, twice a day. A group of 6 normal mice in the same cage was set up as a normal control group (WT). Except for the WT group, they were fed with normal feed, and the rest groups were fed with high-fat feed. The administration was continued for 8 weeks. During the administration, the animal's food intake and body weight were monitored. After the last administration, the animals were fasted for 6 hours and allowed to drink water freely. Then the body weight was measured, the blood was collected from the retro-ocular venous plexus, and liver was dissected. Part of the liver was placed in 4% paraformaldehyde, and the rest was stored in a refrigerator at −80° C. This experiment reflected whether the compound had the treating effect on NAFLD by detecting the levels of liver function indexes ALT and AST in the serum, the contents of TC and TG in the liver, the NAS score of liver pathology (HE staining) and the like.

Figure 4:
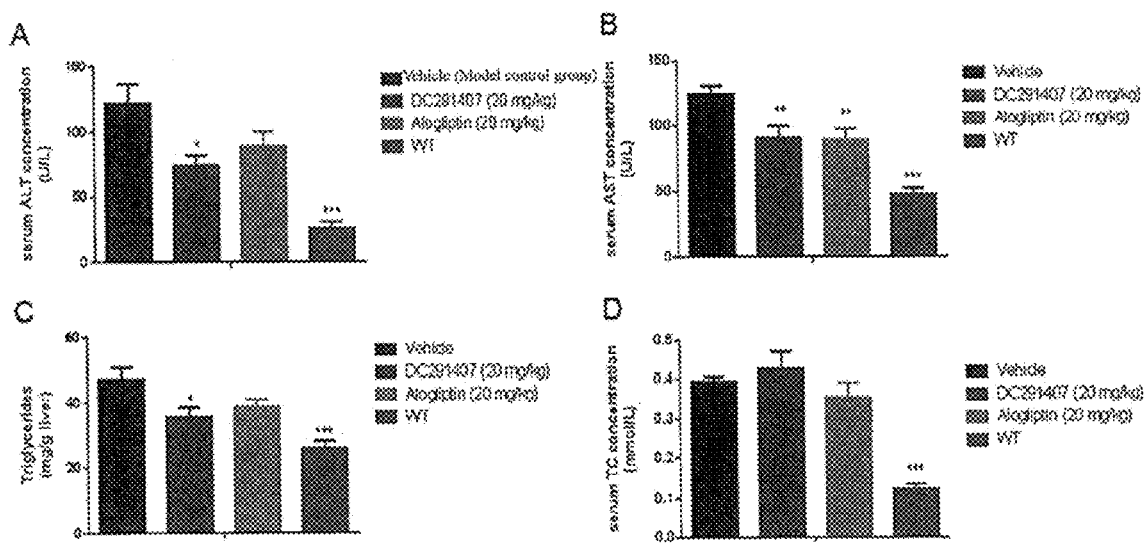
FIG. 4 shows the results of the DPP-4 inhibitor in Example 5 of the present invention on alleviating liver injury blood biochemical indexes and liver triglycerides in high fat-induced non-alcoholic fatty liver disease ob/ob mice model.
Figure 5:
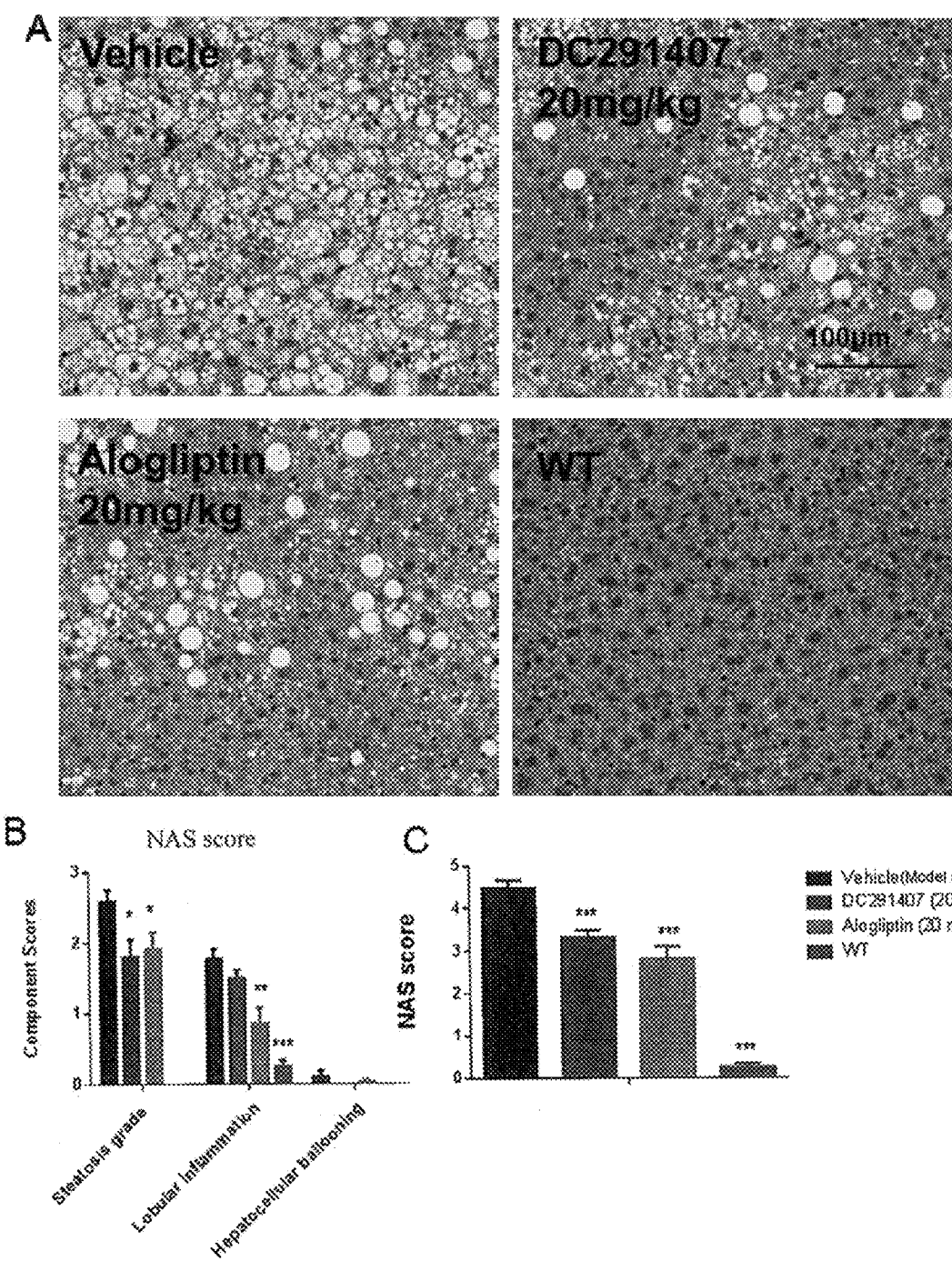
FIG. 5 shows the results of the DPP-4 inhibitor in Example 5 of the present invention on improving liver steatosis and inflammatory pathological indexes in high fat-induced non-alcoholic fatty liver disease ob/ob mice model.

The results showed that DC291407 could significantly reduce the level of ALT and AST in serum and the content of TG in liver tissue after 8 weeks of administration, and its effect was equivalent to that of alogliptin (see FIG. 4); NAS score was performed on HE stained liver pathological sections and the results showed that DC291407 could improve steatosis, its effect was better than that of alogliptin, and had a certain alleviating effect on lobular inflammation, and the overall improvement effect on NAS score was equivalent to that of alogliptin (see FIG. 5).

In summary, the long-term administration of DC291407 significantly improved the liver function of NAFLD model mice, reduced liver steatosis, and had a certain alleviating effect on lobular inflammation.

Example 6 Test of In Vivo Pharmacological Activity on Liver Fibrosis

In this experiment, $CCl_4$-induced liver fibrosis model mice were used to investigate the effect of long-term oral administration of compound DC291407 under multiple doses on liver fibrosis in the model mice, and comparison was conducted with the same dose of sitagliptin.

Animal experiment: Male C57BL/6j mice were injected intraperitoneally with 2 mL/kg, 10% $CCl_4$ (dissolved in olive oil) three times a week to induce liver fibrosis model. Two weeks after modeling, the blood was taken from the retro-ocular venous plexus of the mice, and serum ALT and AST indexes were detected. According to ALT, AST, body weight and other indexes, the mice were randomly divided into 8 groups with 10 mice in each group. There were the models control group (vehicle), DC291407 low-dose group (6 mg/kg), DC291407 middle-dose group (20 mg/kg), DC291407 high-dose group (60 mg/kg), sitagliptin low-dose group (6 mg/kg), Sitagliptin middle-dose group (20 mg/kg), sitagliptin high-dose group (60 mg/kg) and system positive compound OCA group (20 mg/kg). The mice were administered by oral gavage. The OCA group was administered once a day, and the other groups were administered twice a day. During the administration period, the animals' food intake and body weight were monitored. After 3 weeks of administration, the blood was taken from the retro-ocular venous plexus of the mice, and serum ALT and AST indexes were detected. After 6 weeks of administration, the blood was taken from the retro-ocular venous plexus of the mice and then the mice were killed by dislocation. The liver was taken and weighed, part of the liver was fixed with 4% paraformaldehyde, and part of the liver was frozen at −80° C. During the whole experiment, another 10 mice in the same cage were injected intraperitoneally with the same dose of olive oil as a normal control group (WT). This experiment reflected whether the compound had the effect of relieving liver fibrosis by detecting the levels of liver function indexes ALT and AST in serum, the content of hydroxyproline (a characteristic amino acid of collagen) in the liver, and liver pathological changes (Sirius scarlet staining) and the like.

Figure 6:
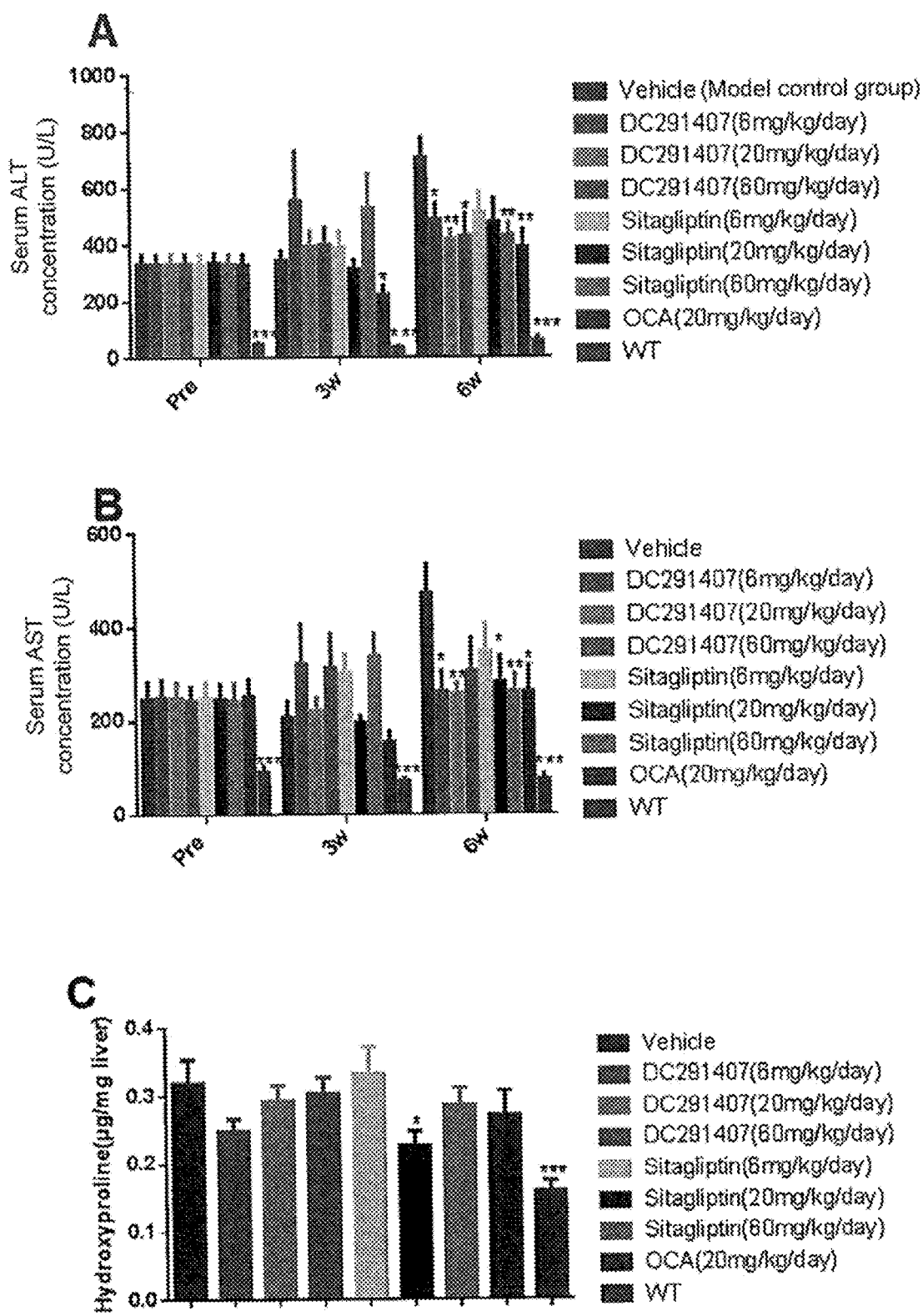
FIG. 6 shows the results of the DPP-4 inhibitor in Example 6 of the present invention on alleviating liver injury blood biochemical indexes and collagen characteristic amino acid indexes in $CCl_4$-induced liver fibrosis model mice.
Figure 7:
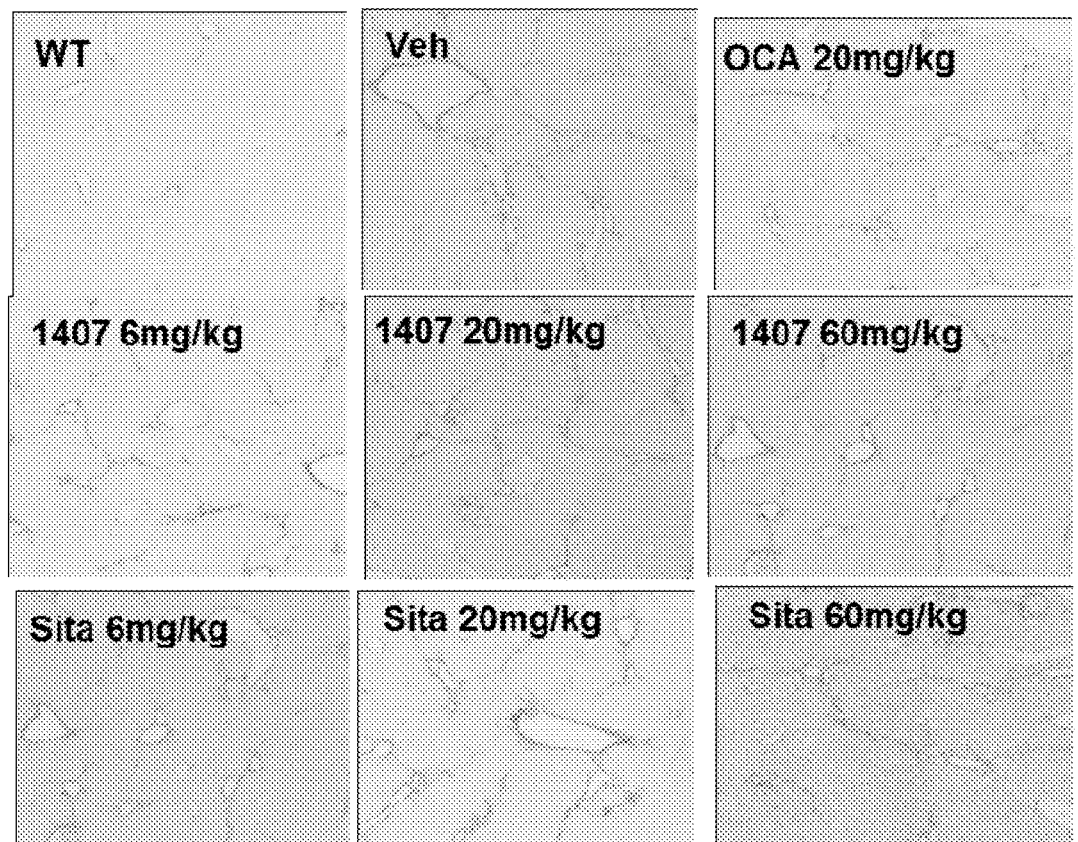
FIG. 7 shows the results of the DPP-4 inhibitor in Example 6 of the present invention on alleviating the pathological indexes of collagen deposition in liver in $CCl_4$-induced liver fibrosis model.
Figure 7:
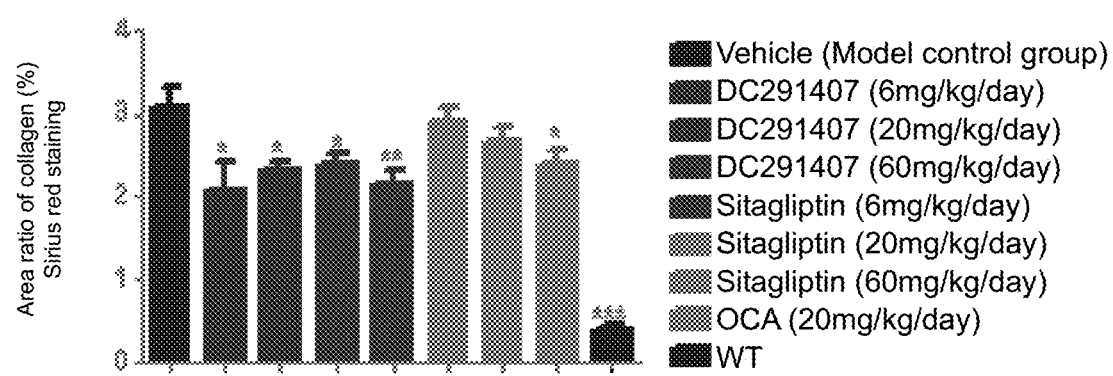

The results of the study showed that the low-dose and medium-dose groups of the compound DC291407 of the present invention could significantly reduce ALT and AST levels in serum after 6 weeks of administration of the compound DC291407, and the high-dose group could significantly reduce the ALT level in serum; the sitagliptin low-dose group had no effect on ALT and AST levels in serum, the middle-dose group significantly reduced the AST level in serum and the high-dose group significantly reduced ALT and AST levels in serum; and the DC291407 low-dose group reduced the content of hydroxyproline in liver tissues without statistics significance (FIG. 6). In the quantitative analysis of liver pathological sections stained with Sirius scarlet, the high, medium and low dose groups of the test compound DC291407 could reduce the collagen content in the liver without dose dependence; only the low dose group of sitagliptin could significantly reduce the collagen content in the liver (FIG. 7).

In summary, long-term administration of the test compound DC291407 in each dose group significantly improved the liver function of $CCl_4$-induced liver fibrosis mice, reduced the deposition of collagen in the liver, and had a certain alleviating effect on liver fibrosis, but no dose dependence was shown in this dose range. All documents mentioned in the present invention are incorporated by reference in this application, as each document is individually incorporated by reference. In addition, it should be understood that after reading the above-mentioned teaching content of the present invention, those skilled in the art can make various changes or modifications to the present invention, and these equivalent forms also fall within the scope defined by the appended claims of the present application.

The invention claimed is:

1. A method for treating liver fibrosis, comprising administering a thieno[3,2-d]pyrimidin-4-one compound represented by the following general formula (I):

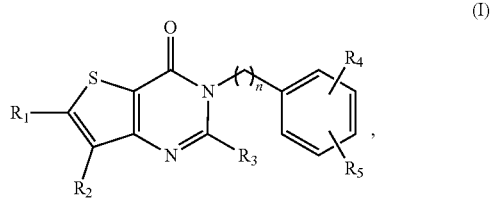

or a pharmaceutically acceptable salt, solvate, stereoisomer, or tautomer thereof to a subject in need thereof, wherein:

n is an integer from 1 to 3;

each of $R_1$ and $R_2$ is independently H or $COOR_8$, provided that $R_1$ and $R_2$ are different;

$R_8$ is H, or linear or branched C1-C6 alkyl;

$R_3$ is

which is a 3-7 membered nitrogen-containing heterocyclic radical, and is substituted by one amino; and each of $R_4$ and $R_5$ is independently H or cyano.

2. The method of claim 1, wherein:

n is 1;

each of $R_1$ and $R_2$ is independently H or $COOR_8$, provided that $R_1$ and $R_2$ are different;

$R_8$ is H or methyl;

$R_3$ is

which is a 3-7 membered nitrogen-containing heterocyclic radical, and is substituted by one amino; and each of $R_4$ and $R_5$ is independently H or cyano, provided that $R_4$ and $R_5$ are different.

3. The method of claim 1, wherein n is 1;

each of $R_1$ and $R_2$ is independently H or $COOR_8$, provided that $R_1$ and $R_2$ are different;

$R_8$ is H, or linear or branched C1-C3 alkyl;

$R_3$ is pyrrolidinyl, piperidinyl, piperazinyl, or homopiperazinyl, and is substituted by one amino; and each of $R_4$ and $R_5$ is independently H or cyano, provided that $R_4$ and $R_5$ are different.

4. The method of claim 1, wherein the thieno[3,2-d]pyrimidin-4-one compound of general formula (I) is selected from the group consisting of:

(DC291407)
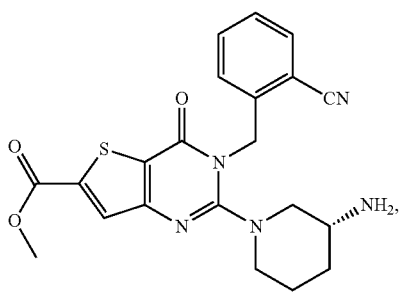

(DC291009)
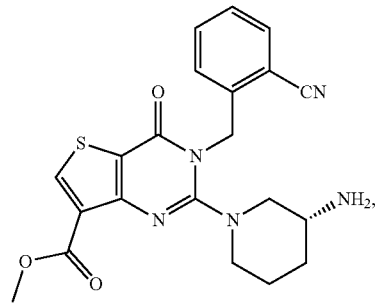

(DC291410)
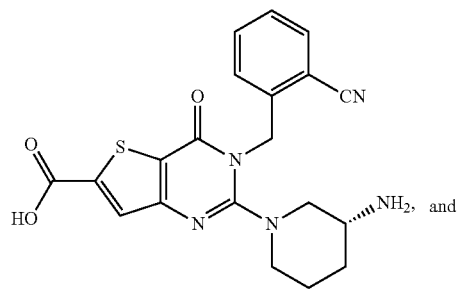
and (DC291002)
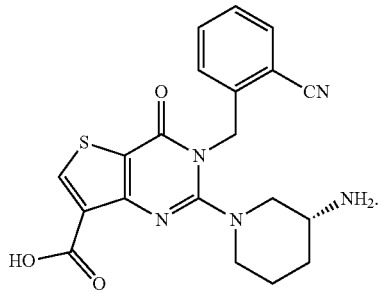

5. The method of claim 1, wherein the thieno[3,2-d]pyrimidin-4-one compound, pharmaceutically acceptable salt, solvate, stereoisomer, or tautomer thereof is administered through a pharmaceutically acceptable carrier.

6. The method of claim 5, wherein the pharmaceutically acceptable carrier is selected from the group consisting of diluent, excipient, filler, binder, wetting agent, disintegrant, absorption promoter, surfactant, adsorption carrier, and lubricant.

7. The method of claim 1, wherein the thieno[3,2-d]pyrimidin-4-one compound, pharmaceutically acceptable salt, solvate, stereoisomer, or tautomer thereof is formulated into a tablet, powder, pill, injection, capsule, film, suppository, ointment or electuary.

8. The method of claim 1, wherein the thieno[3,2-d]pyrimidin-4-one compound, pharmaceutically acceptable salt, solvate, stereoisomer, or tautomer thereof is introduced into the body by injection, spraying, nose drops, eye drops, penetration, absorption, physically or chemically mediated methods.

9. The method of claim 1, wherein the treating is:
(1) down-regulating expression of α-SMA;
(2) down-regulating expression of Col1α1 mRNA;
(3) decreasing deposition of collagen in the liver;
(4) reducing ALT level;
(5) reducing AST level;

(6) reducing content of hydroxyproline in liver tissue; or
(7) inhibiting activation of hepatic stellate cell HSC.

* * * * *